(12) United States Patent
Cobb et al.

(10) Patent No.: US 10,040,819 B2
(45) Date of Patent: *Aug. 7, 2018

(54) CHEMICALLY MODIFYING PEPTIDES

(71) Applicant: The University of Durham, Durham (GB)

(72) Inventors: Steven Cobb, Durham (GB); Christopher Coxon, Durham (GB); Graham Sandford, Durham (GB)

(73) Assignee: The University of Durham, Durham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/312,502

(22) PCT Filed: May 28, 2015

(86) PCT No.: PCT/GB2015/051542
§ 371 (c)(1),
(2) Date: Nov. 18, 2016

(87) PCT Pub. No.: WO2015/181544
PCT Pub. Date: Dec. 3, 2015

(65) Prior Publication Data
US 2017/0081360 A1     Mar. 23, 2017

(30) Foreign Application Priority Data
May 29, 2014 (GB) .................................. 1409536.8

(51) Int. Cl.
*A61K 38/00* (2006.01)
*C07K 1/107* (2006.01)
*C07K 1/08* (2006.01)
*C07K 1/113* (2006.01)
*C07K 1/02* (2006.01)

(52) U.S. Cl.
CPC .............. *C07K 1/1077* (2013.01); *C07K 1/02* (2013.01); *C07K 1/084* (2013.01); *C07K 1/088* (2013.01); *C07K 1/1072* (2013.01); *C07K 1/113* (2013.01)

(58) Field of Classification Search
None
See application file for complete search history.

(56) References Cited

U.S. PATENT DOCUMENTS

2012/0288940 A1   11/2012   Alabugin et al.

FOREIGN PATENT DOCUMENTS

WO   2012117069   9/2012
WO   2012122450   9/2012

OTHER PUBLICATIONS

Spokoyny et al., J. Am. Chem. Soc (2013) 135, 5946-5949.*
Ni et al. The application of an ary hydrazine linker prevents beta-elimination side products in the SPPS of C-terminal cysteine peptides. Published online May 7, 2010. vol. 16, pp. 309-313. (Year: 2010).*
Bernardes et al. Facile Conversion of Cysteines and Alkyl Cysteines to Dehydroalanine on Protein Surfaces: Versatile and Switchable Access to Functionalized Proteins. JACS, 2008. vol. 130, pp. 5052-5053. (Year: 2008).*
Hudson et al., (2013) "Synthesis of a novel tetrafluoropyridine containing amino acid and tripeptide," Tetrahedron Letters 54(36): 4865-4867.
Webster et al., (2014) "A mild method for the synthesis of a novel dehydrobutyrine-containing amino acid," Tetrahedron 70(31): 4661-4667.
Tomkinson et al., (1994) "Use of a Dehydroalanine-Containing Peptide as an Efficient Inhibitor of Tripeptidyl Peptidase II," Archives of Biochemistry and Biophysics, Academic Press, US, 314(2): 279-279.
Li and Xu et al., (2000) "1-Ethyl 2-Halopyridinium Salts, Highly Efficient Coupling Reagents for Hindered Peptide Synthesis both in Solution and the Solid-Phase," Tetrahedron 56: 8119-8131.

* cited by examiner

*Primary Examiner* — Marcela M Cordero Garcia
(74) *Attorney, Agent, or Firm* — Rudy J. Ng; Bozicevic, Field & Francis LLP

(57) ABSTRACT

A method for chemically modifying a peptide, derivative or analogue thereof is described. The method comprises contacting a peptide, derivative or analogue thereof with a fluoro-heteroaromatic compound to activate the peptide, derivative or analogue thereof. The activated peptide, derivative or analogue thereof is then contacted with a nucleophile or base to create a chemically modified peptide, derivative or analogue thereof.

26 Claims, 7 Drawing Sheets

Figure 10

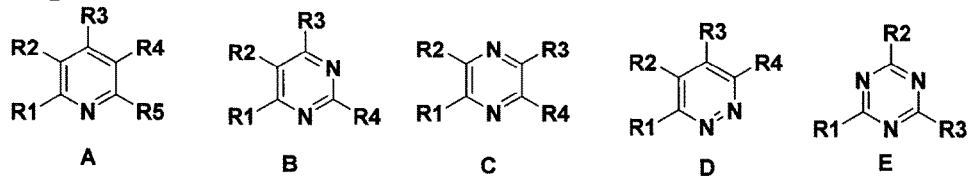

R1 = H, F, Br, Cl, $CH_3$, CN, $OCH_3$, $NH_2$, NHR, $CF(CF_3)_2$, $CF_3$, $SO_2Ph$, $NO_2$
R2 = H, F, Br, Cl, $CH_3$, CN, $OCH_3$, $NH_2$, NHR, $CF(CF_3)_2$, $CF_3$, $SO_2Ph$, $NO_2$
R3 = H, F, Br, Cl, $CH_3$, CN, $OCH_3$, $NH_2$, NHR, $CF(CF_3)_2$, $CF_3$, $SO_2Ph$, $NO_2$
R4 = H, F, Br, Cl, $CH_3$, CN, $OCH_3$, $NH_2$, NHR, $CF(CF_3)_2$, $CF_3$, $SO_2Ph$, $NO_2$
R5 = H, F, Br, Cl, $CH_3$, CN, $OCH_3$, $NH_2$, NHR, $CF(CF_3)_2$, $CF_3$, $SO_2Ph$, $NO_2$

Figure 11

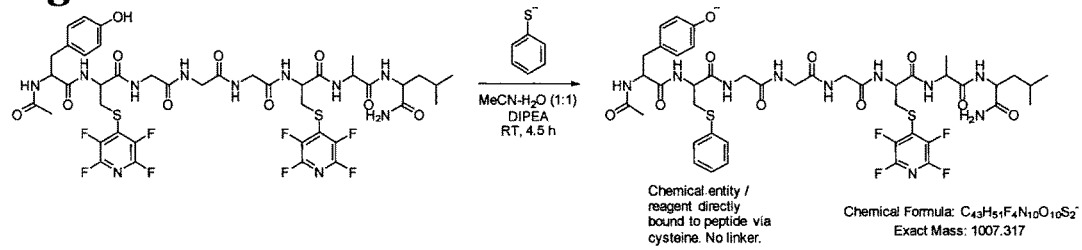

Chemical entity / reagent directly bound to peptide via cysteine. No linker.

Chemical Formula: $C_{43}H_{51}F_4N_{10}O_{10}S_2^-$
Exact Mass: 1007.317

Figure 12

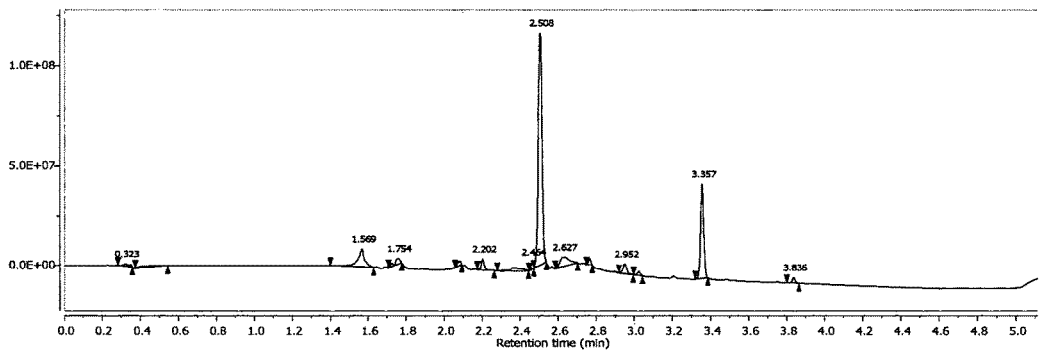

CHEMICALLY MODIFYING PEPTIDES

CROSS-REFERENCE TO RELATED APPLICATIONS

This application is the U.S. national phase under 35 U.S.C. § 371 of PCT International Application No. PCT/GB215/051542, which has an international filing date of May 28, 2015 and designed the United States of America, which application claims benefit of priority of GB Application No. 1409536.8, filed May 29, 2014, the disclosures of each of which are incorporated by reference herein.

The present invention relates to a method for chemically modifying peptides, derivatives and analogues thereof. More specifically, the invention relates to the traceless chemical modification of peptides and peptidomimetics, derivatives or analogues thereof.

Chemical modifications can be used to modulate a variety of protein and peptide properties. For example, the bioconjugation of polyethylene glycol (PEG) to proteins (i.e. PEGylation) is routinely used to increase protein solubility and bioavailability. Many of the bioconjugation methods employed to date utilize the nucleophilic character of the thiol group present on the side chain of cysteine. This provides an excellent chemical handle for the attachment of a range of chemical entities such as PEG groups, other biomolecules, including sugars and DNA, and fluorescent probes. Many of the approaches that are currently used for chemical modification of peptide and proteins involve conjugating the desired chemical entity to the peptide/protein using a linker. Because a linker molecule is used, the peptide/protein is not directly attached to the chemical entity that is introduced. A problem with this is that often the linkers that are used produce more than one product (poor control of regio- and stereo-isomer formation), which presents a significant challenge in terms of purification and characterization of the peptide/protein conjugate. Additionally, the presence of a linker can often have an adverse effect on peptide-conjugate biological properties, such as binding to an enzyme or protein target.

There is a considerable amount of prior art concerning bioconjugation of chemical entities on to peptides and proteins. For example, ThioLogics Ltd has developed technology for selective protein tagging. However, this technology uses linkers, which suffers from the problem that the peptide or protein is not directly linked to the chemical entity that is introduced. ThioLogics Ltd have published a number of papers relating to their technology. These include: Castañeda, L, Maruani, A, Schumacher, F F, Miranda, E, Chudasama, V, Chester, K A, Baker, J R, Smith, M E B, Caddick, S. *Chem Comm*, 2013, 49, 8187-8189; Castañeda L, Wright Z V F, Marculescu C, Tran, T M, Chudasama V, Maruani A, Hull, E A, Nunes J P M, Fitzmaurice R J, Smith M E B, Jones L H, Caddick S, Baker J R. *Tetrahedron Lett*, 2013, 54, 3493-3495; Nathani R I, Chudasama V, Ryan C P, Moody P R, Morgan R E, Fitzmaurice R J, Smith, M E B, Baker J, Caddick S. *Org Biomol Chem*, 2013, 2408-2411; Ryan, C. P., Smith, M. E. B., Schumacher, F. F., Grohmann, D., Papaioannou, D., Waksman, G., Werner, F., Baker, J. R., Caddick, S. *Chem Commun*, 2011, 47, 5452-5454.; Chudasama V, Smith M E, Schumacher F F, Papaioannou D, Waksman G, Baker J R, Caddick S. *Chem Commun*, 2011, 47, 8781-8783; and Mark E. B. Smith, Felix F. Schumacher, Christopher P. Ryan, Lauren M. Tedaldi, Danai Papaioannou, Gabriel Waksman, Stephen Caddick and James R. Baker *J. Am. Chem. Soc.*, 2010, 132, 1960.

The Davis group at Oxford are another example of a researchers who have undertaken research into bioconjugation of chemical entities on to peptides and proteins where the cysteine residues are targeted, as described in "A 'Tag-and-Modify' Approach to Site-Selective Protein Modification" J. M. Chalker, G. J. L. Bernardes, B. G. Davis *Acc. Chem. Res.*, 2011, 44, 730-41. One approach they use results in a disulfide linkage being present in the final product. A problem with this approach is that it is less stable than a direct covalent link between the nucleophile of the peptide or proein and the carbon atom of the bioconjugate. A second approach used by the Davis group and others involves the formation of a dehydroalanine intermediate. This intermediate destroys the alpha-chirality of the amino acids involved and gives rise to the formation of isomeric products. A range of chemical entities can be attached using this method. It would be advantageous to be able to attach the same range of chemical entities while controlling the isomers that are formed. However, in other cases dehydroalanine intermediates can be useful in circumstances where the alpha-chirality is not important. For this reason, it would be advantageous to have additional methods which allow the production of these dehydroalanine intermediates. Given the importance of these intermediates, it would also be advantageous to have a method of production which allowed the reaction pathway for their formation to be monitored in-situ.

The current invention arises from the inventors' work in trying to overcome the problems associated with the prior art. The inventors have now developed a new technology platform that allows chemical moieties to be attached to a peptide or protein in a manner that does not involve a linker. Additionally, the inventors found a novel method for the manufacture of dehydroalanine intermediates. They have found that a peptide containing a halogenated heteroaromatic group can serve as a suitable substrate for traceless chemical modification via nucleophilic displacement or elimination of the halogenated heteroaromatic group. This approach can be used to create chemically modified peptides, derivatives or analogues thereof. In certain embodiments an introduced chemical entity is directly bound to the peptide, derivative or analogue thereof.

Thus, according to a first aspect of the invention, there is provided a method for chemically modifying a peptide, derivative or analogue thereof, the method comprising:
(i) contacting a peptide, derivative or analogue thereof with a fluoro-heteroaromatic compound to activate the peptide, derivative or analogue thereof; and
(ii) contacting the activated peptide, derivative or analogue thereof with a nucleophile or base to create a chemically modified peptide, derivative or analogue thereof.

In a second aspect, there is provided use of a fluoro-heteroaromatic compound to activate a peptide, derivative or analogue thereof, thereby allowing the creation of a chemically modified peptide, derivative or analogue thereof.

Advantageously, the method of the first aspect allows selective functionalisation of the peptide, derivative or analogue thereof. The term "selective functionalisation" can mean that specific amino acid residues in the peptide are functionalised.

Preferably, the peptide comprises at least two, three, four or five amino acid residues. Preferably, the peptide comprises a polypeptide. Preferably, the polypeptide comprises at least five, ten or fifteen amino acid residues.

The term "derivative or analogue thereof" can mean that the amino acids residues of the peptide are replaced by residues (whether natural amino acids, non-natural amino acids or amino acid mimics) with similar side chains or peptide backbone properties. Additionally, the terminals of such peptides may be protected by N- and C-terminal protecting groups with similar properties to acetyl or amide groups.

Derivatives and analogues of peptides according to the invention may also include those that increase the peptide's half-life in vivo. For example, a derivative or analogue of the peptides of the invention may include peptoid and retropeptoid derivatives of the peptides, peptide-peptoid hybrids and D-amino acid derivatives of the peptides.

Peptoids, or poly-N-substituted glycines, are a class of peptidomimetics whose side chains are appended to the nitrogen atom of the peptide backbone, rather than to the alpha-carbons, as they are in amino acids. Peptoid derivatives of the peptides of the invention may be readily designed from knowledge of the structure of the peptide. A retropeptoid is expected to bind in the opposite direction in the ligand-binding groove, as compared to a peptide or peptoid-peptide hybrid containing one peptoid residue. As a result, the side chains of the peptoid residues are able point in the same direction as the side chains in the original peptide.

Preferably, the fluoro-heteroaromatic compound contains at least one nitrogen atom in its aromatic ring. The fluoro-heteroaromatic compound may contain one, two or three nitrogen atoms in the aromatic ring. Accordingly, the fluoro-heteroaromatic compound may comprise a fluoropyridine, a fluoropyrazine, a fluoropyrimidine, a fluoropyridazine or a fluorotriazine. In one preferred embodiment, the fluoro-heteroaromatic compound comprises a fluoropyridine. In an alternative preferred embodiment, the fluoro-heteroaromatic compound comprises a fluoropyrimidine or a fluoropyridazine.

The fluoro-heteroaromatic compound may comprise a fused six-membered ring. Accordingly, the fluoro-heteroaromatic may comprise a fluoroquinoline, a fluoroisoquinoline, a fluoroquinoxaline, a fluoroquinazoline, a fluorocinnoline, a fluorophthalazine or a fluoroacridine. Preferably, the fluoro-heteroaromatic compound comprises a fluoroquinoline.

Preferably, the fluoro-heteroaromatic compound contains at least two halogen atoms, wherein at least one of the halogen atoms is a fluorine atom, and each halogen atom is covalently bonded to a carbon atom in the aromatic ring.

Accordingly, in embodiments where the heteroaromatic compound comprises one six-membered ring which contains one nitrogen atom in the aromatic ring then it may contain two, three, four or five halogen atoms, wherein each halogen atom is bonded to a carbon atom in its aromatic ring. In embodiments where the heteroaromatic compound one six-membered ring which contains two nitrogen atoms in the aromatic ring then it may contain two, three or four halogen atoms, wherein each halogen atom is bonded to a carbon atom in its aromatic ring. In embodiments where the heteroaromatic compound one six-membered ring which contains three nitrogen atoms in the aromatic ring then it may contain two or three halogen atoms, wherein each halogen atom is bonded to a carbon atom in its aromatic ring.

In one preferred embodiment, the at least two halogen atoms only comprise fluorine atoms.

In embodiments where the heteroaromatic compound comprises one six-membered ring which contains one nitrogen atom in the aromatic ring then it may contain one, two, three, four or five fluorine atoms, wherein each fluorine atom is bonded to a carbon atom in its aromatic ring. In embodiments where the heteroaromatic compound comprises one six-membered ring which contains two nitrogen atoms in the aromatic ring then it may contain one, two, three or four fluorine atoms, wherein each fluorine atom is bonded to a carbon atom in its aromatic ring. In embodiments where the heteroaromatic compound comprises one six-membered ring which contains three nitrogen atoms in the aromatic ring then it may contain one, two or three fluorine atoms, wherein each fluorine atom is bonded to a carbon atom in its aromatic ring.

In one embodiment, the fluoro-heteroaromatic compound comprises at least one hydrogen atom, wherein each hydrogen atom is covalently bonded to a carbon atom in the aromatic ring. Preferably, the fluoro-heteroaromatic compound comprises 2,4,6-trifluoropyridine or 2,3,4,6-tetrafluoropyridine.

In a preferred embodiment, therefore, the fluoro-heteroaromatic compound comprises a perfluoroaromatic compound. Preferably, the fluoro-heteroaromatic compound comprises perfluoropyridine, perfluoropyridazine or perfluoroquinoline.

In another preferred embodiment, the fluoro-heteroaromatic compound comprises a pentafluoroaromatic compound, most preferably pentafluoropyridine.

Alternatively, the at least two halogen atoms may comprise at least one chlorine atom, at least one bromine atom and/or at least one iodine atom.

In an alternative preferred embodiment, the at least two halogen atoms comprise at least one fluorine atom and at least one chlorine atom.

The heteroaromatic compound may comprise 1, 2, 3 or 4 chlorine atoms, wherein each chlorine atom is bonded to a carbon atom in its aromatic ring.

In another preferred embodiment, the fluoro-heteroaromatic compound comprises a chloro-fluoro-heteroaromatic compound, most preferably 3,5-dichloro-2,4,6-trifluoropyridine, 3-chloro-2,4,5,6-tetrafluoropyridine, 2,3,4,5-tetrachloro-6-fluoropyridine or 5-chloro-2,4,5-trifluoropyrimidine.

Preferably, the peptide, derivative or analogue thereof contains at least one nucleophilic side chain. Preferably, the nucleophilic side chain reacts in an $S_NAr$ type reaction with the fluoro-heteroaromatic compound to displace a fluorine atom and create a covalent bond between the nucleophilic side chain and the heteroaromatic compound.

Advantageously, and preferably, the peptide or derivative or analogue thereof is activated in step (i) due to the formation of a leaving group on the peptide, derivative or analogue thereof. Preferably, the leaving group comprises the heteroaromatic compound, which is covalently bonded to the nucleophilic side chain, and at least a portion of the nucleophilic side chain.

Alternatively, the peptide or derivative or analogue thereof is activated in step (i) due to the formation of a linker group, wherein the linker group is configured to link the peptide to at least two tags. Preferably, the linker group comprises the heteroaromatic compound, which is covalently bonded to the nucleophilic side chain.

Preferably, step (i) of the method comprises dissolving a peptide, derivative or analogue thereof in a solvent, and adding a base thereto before the fluoro-heteroaromatic compound is added to the dissolved peptide to create a reaction solution. Preferably, the base is N,N-diisopropylethylamine (DIPEA). Preferably the solvent is 2,2,2-trifluoroethanol (TFE).

Preferably, the reaction solution is mixed (e.g. by shaking) for at least one hour. Preferably, the step of mixing the solution lasts for at least two hours. Further preferably, the step of mixing the solution lasts for at least three hours.

Further preferably, the step of mixing the solution lasts for at least four hours. Further preferably, the step of mixing the solution lasts for at least five hours.

Preferably, the step of mixing the solution is undertaken at room temperature. Alternatively, the step of mixing the solution is undertaken at at least 30° C. and preferably at least 40° C., and further preferably at least 50° C.

Optionally, once the above steps have been completed the solution may be subjected to a vacuum to remove any volatile liquids.

Preferably, the molar ratio of the peptide, derivative or analogue thereof to the fluoro-heteroaromatic compound in step (i) is between 1:1 and 1:100. More preferably, the molar ratio in step (i) is between 1:5 and 1:50, or even more preferably between 1:10 and 1:40, and most preferably between 1:20 and 1:30.

In one preferred embodiment, step (ii) of the method comprises contacting the activated peptide, derivative or analogue thereof with a nucleophile. Preferably, the nucleophile displaces the leaving group and creates a covalent bond between the activated peptide, derivative or analogue thereof and the nucleophile.

Advantageously, the method is traceless, i.e. no trace of the fluoro-heteroaromatic compound remains bonded to the portion of the peptide, derivative or analogue thereof which is chemically modified, and the portion of the peptide, derivative or analogue thereof which is chemically modified will comprise at least the amino acid, derivative or analogue thereof which included the nucleophilic side chain.

Advantageously, as no linker is necessary to chemically modify the peptide, derivative or analogue thereof, it is possible to control the regio- and stereo-isomers produced. Hence, the method does not adversely affect the stereochemistry of the peptide, derivative or analogue thereof, and is less invasive. As no linker is involved naturally occurring peptides may be accessed.

In an alternative embodiment, step (ii) of the method comprises contacting the activated peptide, derivative or analogue thereof with at least two nucleophilic molecules. Preferably, the nucleophilic molecules displace two or more halogens on the heteroaromatic compound.

Advantageously, as multiple chemical entities are attached binding interactions to specific biological targets can be enhanced. For example in the application of attaching multiple sugars to the activated peptide binding to carbohydrate mediate cell surface receptors can be enhanced. In addition the approach will allows for two or more PEG groups to be attached to the activated peptide thus enabling additional flexibility in tuning the cellular delivery and in vivo stability of the system.

Preferably, step (ii) of the method comprises adding a nucleophile to a solution containing the activated peptide to create a reaction solution. Preferably, the solvent which comprises the solution, is Acetonitrile (MeCN) and/or water.

Preferably, the reaction solution is mixed (e.g. by shaking) for at least one hour. Preferably, the step of mixing the solution lasts for at least two hours. Further preferably, the step of mixing the solution lasts for at least three hours. Further preferably, the step of mixing the solution lasts for at least four hours. Further preferably, the step of mixing the solution lasts for at least five hours.

Preferably, the step of mixing the solution is undertaken at room temperature. Alternatively, the step of mixing the solution is undertaken at at least 30° C. and preferably at least 40° C., and further preferably at least 50° C.

Preferably, the molar ratio of the activated peptide, derivative or analogue thereof to the nucleophile in step (ii) is between 1:1 and 1:100. More preferably, the molar ratio in step (ii) is between 1:5 and 1:10, or even more preferably between 1:10 and 1:40, and most preferably between 1:20 and 1:30.

In one embodiment in which the activated peptide, derivative or analogue thereof is contacted with a nucleophile or at least two nucleophilic molecules, at least one of the nucleophilic side chains preferably comprises a thiol group. The or each thiol may be provided on a cysteine residue or modified cysteine residue in the peptide, derivative or analogue thereof.

In another embodiment in which the activated peptide, derivative or analogue thereof is contacted with a nucleophile or at least two nucleophilic molecules, at least one of the nucleophilic side chains preferably comprises an amine group, wherein the amine group preferably comprises a primary amine or secondary amine. The or each amine group may be provided on any amino acid residue within the peptide, derivative or analogue thereof. For example, the or each amine group may be provided on a lysine residue in the peptide, derivative or analogue thereof.

In yet another embodiment in which the activated peptide, derivative or analogue thereof is contacted with a nucleophile or at least two nucleophilic molecules, at least one of the nucleophilic side chains preferably comprises an alcohol group, wherein the alcohol group preferably comprises a phenol group. The or each alcohol group may be provided on a serine or threonine residue within the peptide, derivative or analogue thereof. Preferably, the or each alcohol group may be provided on a serine residue in the peptide, derivative or analogue thereof.

In a further embodiment in which the activated peptide, derivative or analogue thereof is contacted with a nucleophile or at least two nucleophilic molecules, at least one of the nucleophilic side chains preferably comprises a selenol group. The or each selenol group may be provided on a selenocysteine residue within the peptide, derivative or analogue thereof.

Preferably, in an embodiment in which the activated peptide, derivative or analogue thereof is contacted with a nucleophile or at least two nucleophilic molecules, the nucleophile or the nucleophilic molecules comprise an organic molecule possessing nucleophilic functionality.

Preferably, in an embodiment in which the activated peptide, derivative or analogue thereof is contacted with a nucleophile or at least two nucleophilic molecules, the nucleophile may include at least one group possessing nucleophilic functionality, which may be selected from a thiol group, a hydroxyl group, an amine group and a selenol group. In embodiments in which the nucleophilic group is an amine group, the amine group preferably comprises a primary amine or a secondary amine.

In embodiments in which the group possessing nucleophilic functionality is a thiol group, the nucleophile may comprise a thiol containing sugar, a thiol containing nucleoside, a thiol containing alkyl chain, a thiol containing PEGylating agent, a thiol containing fluorescent tag or a thiol containing antibody.

In embodiments in which the group possessing nucleophilic functionality is a hydroxyl group, the nucleophile may comprise a hydroxyl containing sugar, a hydroxyl containing nucleoside, a hydroxyl containing alkyl chain, a hydroxyl containing PEGylating agent, a hydroxyl containing fluorescent tag or a hydroxyl containing antibody.

In embodiments in which the group possessing nucleophilic functionality is an amine group, the nucleophile may comprise an amine containing sugar, an amine containing nucleoside, an amine containing alkyl chain, an amine containing PEGylating agent, an amine containing fluorescent tag or an amine containing antibody.

In embodiments in which the group possessing nucleophilic functionality is a selenol group, the nucleophile may comprise a selenol containing sugar, a selenol containing nucleoside, a selenol containing alkyl chain, a selenol containing PEGylating agent, a selenol containing fluorescent tag or a selenol containing antibody.

Preferably, the nucleophile is glutathione.

Preferably, in an embodiment in which the activated peptide, derivative or analogue thereof is contacted with a nucleophile the chemical modification may comprise conjugation of a chemical entity onto the peptide. Preferably, the chemical entity is selected from a group consisting of a sugar, a nucleoside, an alkyl chain, PEG, a fluorescent tag and an antibody. Where the chemical moiety is a sugar it will preferably comprise a thiosugar.

In another embodiment of the method, step (ii) comprises contacting the activated peptide, derivative or analogue thereof with a base. Preferably, the activated peptide, derivative or analogue thereof undergoes an elimination reaction resulting in the formation of a dehydroalanine-containing peptide, derivative or analogue thereof. Advantageously, as with the method which uses a nucleophile in step (ii), use of a base is also traceless.

Preferably, step (ii) of the method comprises adding a base to a solution containing the activated peptide to create a reaction solution. Preferably the solvent which comprises the solution is Acetonitrile (MeCN) and/or water.

Preferably, the reaction solution is mixed (e.g. by shaking) for at least one hour. Preferably, the step of mixing the solution lasts for at least two hours. Further preferably, the step of mixing the solution lasts for at least three hours. Further preferably, the step of mixing the solution lasts for at least four hours. Further preferably, the step of mixing the solution lasts for at least five hours.

Preferably, the step of mixing the solution is undertaken at room temperature. Alternatively, the step of mixing the solution is undertaken at at least 30° C. and preferably at least 40° C., and further preferably at least 50° C.

Preferably, the molar ratio of the activated peptide, derivative or analogue thereof to the base in step (ii) is between 1:1 and 1:100. More preferably, the molar ratio in step (ii) is between 1:5 and 1:50, or even more preferably between 1:10 and 1:40, and most preferably between 1:20 and 1:30.

In one embodiment in which the activated peptide, derivative or analogue thereof is contacted with a base, at least one of the nucleophilic side chains preferably comprises a thiol group. The or each thiol may be provided on a cysteine residue or modified cysteine residue in the peptide, derivative or analogue thereof.

In another embodiment in which the activated peptide, derivative or analogue thereof is contacted with a base, at least one of the nucleophilic side chains preferably comprises a selenol group. The or each selenol group may be provided on a selenocysteine residue within the peptide, derivative or analogue thereof.

In yet another embodiment in which the activated peptide, derivative or analogue thereof is contacted with a base, at least one of the nucleophilic side chains preferably comprises an alcohol group, wherein the alcohol group preferably comprises a phenol group. The or each alcohol group may be provided on a serine or threonine residue within the peptide, derivative or analogue thereof. Preferably, the or each alcohol group may be provided on a serine residue in the peptide, derivative or analogue thereof.

The base may comprise an inorganic base or an organic base.

Preferably, the base is potassium thioacetate.

Preferably, in an embodiment in which the activated peptide, derivative or analogue thereof is contacted with a base, an additional step is carried out, subsequent to step (ii), the step comprising further reacting the dehydroalanine-containing peptide, derivative or analogue thereof to attach a chemical entity to the peptide.

Preferably, the chemical entity is selected from a group consisting of a sugar, a nucleoside, an alkyl chain, PEG, a fluorescent tag and an antibody. Where the chemical moiety is a sugar it will preferably comprise a thiosugar.

Preferably, the additional step of the method comprises dissolving the dehydroalanine-containing peptide, derivative or analogue thereof in a solvent, and adding a nucleophile thereto to create a reaction solution. Preferably the solvent is an organic solvent. The organic solvent may comprise dimethylformamide (DMF). Alternatively, the solvent may be water.

Preferably, the reaction solution is mixed (e.g. by shaking) for at least one hour. Preferably, the step of mixing the solution lasts for at least two hours. Further preferably, the step of mixing the solution lasts for at least three hours. Further preferably, the step of mixing the solution lasts for at least four hours. Further preferably, the step of mixing the solution lasts for at least five hours.

Preferably, the step of mixing the solution is undertaken at room temperature. Alternatively, the step of mixing the solution is undertaken between a temperature range of 0° C. to 150° C., preferably between 20° C. to 100° C.

Preferably, the molar ratio of the dehydroalanine-containing peptide, derivative or analogue thereof to the nucleophileis between 1:1 and 1:100. More preferably, the molar ratio in step (i) is between 1:5 and 1:50, or even more preferably between 1:10 and 1:40, and most preferably between 1:20 and 1:30.

The nucleophile may include at least one group possessing nucleophilic functionality, which may be selected from a thiol group, a hydroxyl group, an amine group and a selenol group. In embodiments in which the nucleophilic group is an amine group, the amine group preferably comprises a primary amine or a secondary amine.

In embodiments in which the group possessing nucleophilic functionality is a thiol group the nucleophile may comprise a thiol containing sugar, a thiol containing nucleoside, a thiol containing alkyl chain, a thiol containing PEGylating agent, a thiol containing fluorescent tag or a thiol containing antibody.

In embodiments in which the group possessing nucleophilic functionality is a hydroxyl group the nucleophile may comprise a hydroxyl containing sugar, a hydroxyl containing nucleoside, a hydroxyl containing alkyl chain, a hydroxyl containing PEGylating agent, a hydroxyl containing fluorescent tag or a hydroxyl containing antibody.

In embodiments in which the group possessing nucleophilic functionality is an amine group the nucleophile may comprise an amine containing sugar, an amine containing nucleoside, an amine containing alkyl chain, an amine containing PEGylating agent, an amine containing fluorescent tag or an amine containing antibody.

In embodiments in which the group possessing nucleophilic functionality is a selenol group the nucleophile may comprise a selenol containing sugar, a selenol containing nucleoside, a selenol containing alkyl chain, a selenol containing PEGylating agent, a selenol containing fluorescent tag or a selenol containing antibody.

According to a third aspect of the invention, there is provided a chemically modified peptide, derivative or analogue thereof obtained or obtainable by the method according to the first aspect of the invention.

The chemically modified peptide, derivative or analogue thereof may be functionalised or tagged with a selected chemical entity. For example, the chemical entity may be selected from a group consisting of a sugar, a nucleoside, an alkyl chain, PEG, a fluorescent tag and an antibody. Where the chemical moiety is a sugar it will preferably comprise a thiosugar.

According to a fourth aspect of the present invention, there is provided a dehydroalanine-containing peptide, derivative or analogue thereof, the dehydroalanine-containing peptide, derivative or analogue thereof obtained according to the method of the first aspect of the invention.

The inventors have found that incorporation into the peptide, derivative or analogue thereof of a fluoro-heteroaromatic group provides a very useful functional group that enables both $^{19}$F NMR analysis and further chemical modification.

Hence, in a fifth aspect, there is provided use of $^{19}$F NMR to monitor the method according to the first aspect of the invention.

This allows in-situ real-time monitoring of the reaction pathway and, given the properties of $^{19}$F NMR, precise structural information can also be obtained. Monitoring may involve analysis by $^{19}$F NMR to analyze whether the desired products have formed, checking to see if any additional products have formed, and/or checking to see if any unreacted reagents are present. Advantageously, this form of monitoring can be carried out using the crude reaction mixture without the need for a work-up or purification step.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:

FIG. 10 shows various embodiments of suitable fluoro-heteroaromatic compounds which can be reacted with a peptide, derivative or analogue thereof to create an activated peptide, derivative or analogue thereof according to the invention;

FIG. 11 shows the reaction of Peptide 2 with thiophenolate;

FIG. 12 is the liquid chromatography-mass spectrometry (LCMS) spectrum for the crude reaction mixture resulting from the reaction shown in FIG. 12;

EXAMPLES

As mentioned previously, it is desirable to be able to chemically modify peptides, analogues and derivatives thereof. It is often desirable to chemically modify a peptide, analogue or derivative thereof by attaching a chemical entity to the said peptide, analogue or derivative thereof. Much work has been done in developing this process in the prior art.

Figure 1:
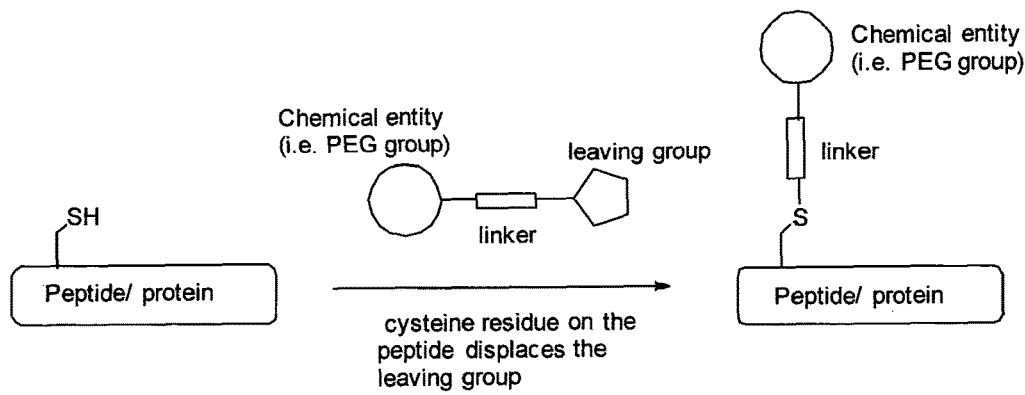
FIG. 1 is a schematic diagram showing the common method used in the prior art for chemical modification of a protein or peptide, where a chemical entity is conjugated to a protein or peptide using a linker.

One method developed in the prior art involves linking the peptide, analogue or derivative thereof to the chemical entity by means of a linker. A schematic showing how this can be achieved is shown in FIG. 1 and examples using linkers developed by ThioLogics are shown in FIGS. 5, 6, 7, 8 and 9. As discussed above, linkers that are used often produce more than one product (poor control of regio- and stereo-isomer formation) which presents a significant challenge in terms of purification and characterization.

Figure 3:
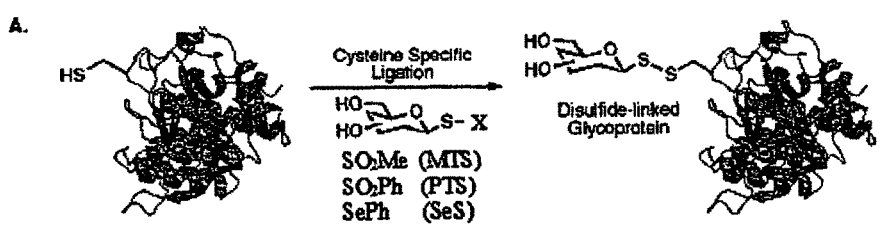
FIG. 3 shows one approach for chemical modification of a protein or peptide used in the prior art, where a disulfide bond is present in the final product.
Figure 4:
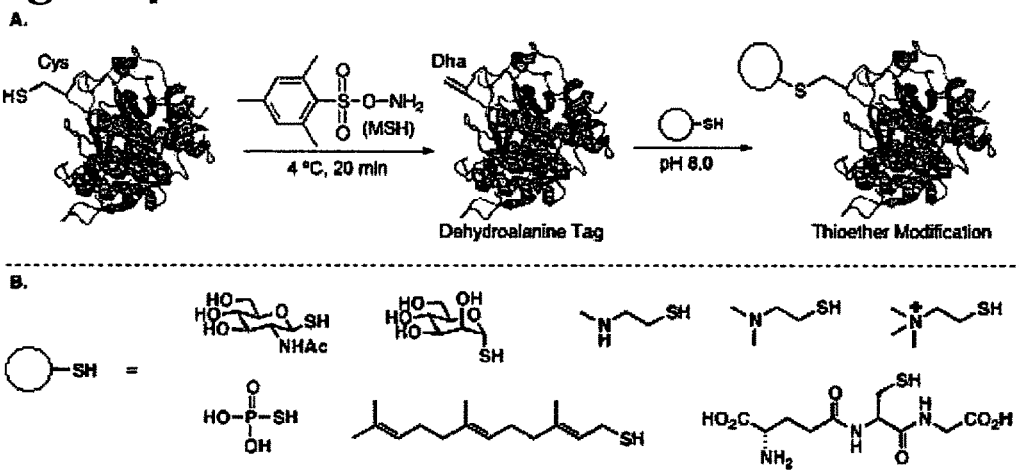
FIG. 4 shows an alternative approach for chemical modification of a protein or peptide used in the prior art, where the alpha-chirality of the amino acids involved is racemised.
Figure 5:
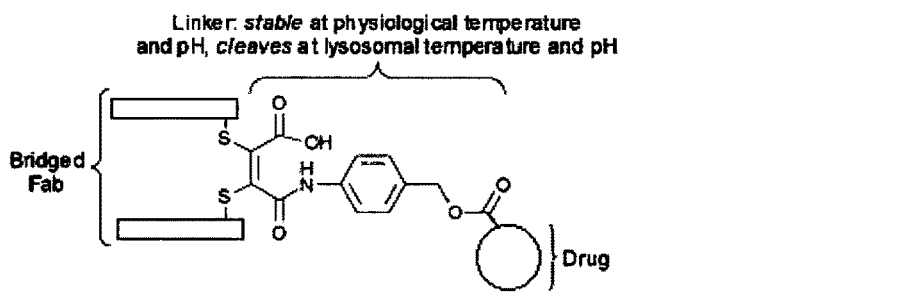
FIG. 5 shows a linker used in the prior art for homogeneous antibody-drug conjugation.
Figure 6:
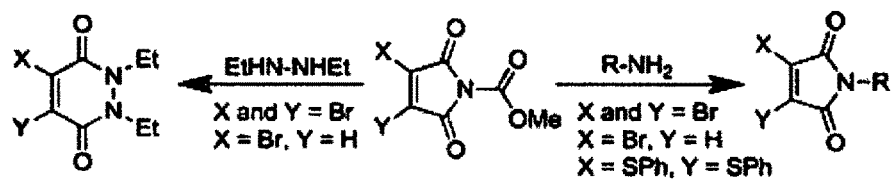
FIG. 6 shows a molecule developed in the prior art for use as a linker.
Figure 7:
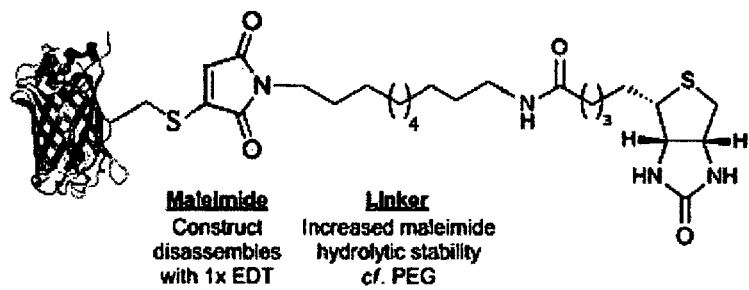
FIG. 7 shows a protein which has been chemically modified, using a linker, according to the teachings of the prior art.
Figure 8:
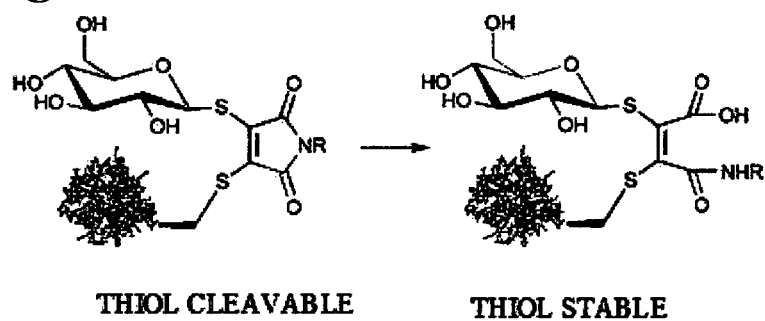
FIG. 8 shows how a protein can be chemically modified, using maleimide as a linker, according to the teachings of the prior art.
Figure 9:
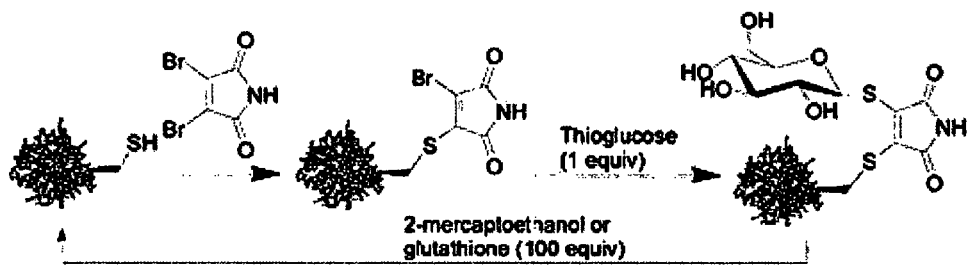
FIG. 9 shows how a protein can be chemically modified, using bromomaleimide as a linker, according to the teachings of the prior art.

Alternatively, the Davis group at Oxford have devised an approach that results in a disulfide linkage being present in the final product, as shown in FIG. 3, or involves the formation of a dehydroalanine intermediate, as shown in FIG. 4. Drawbacks with both of these approaches are discussed above.

Figure 2:
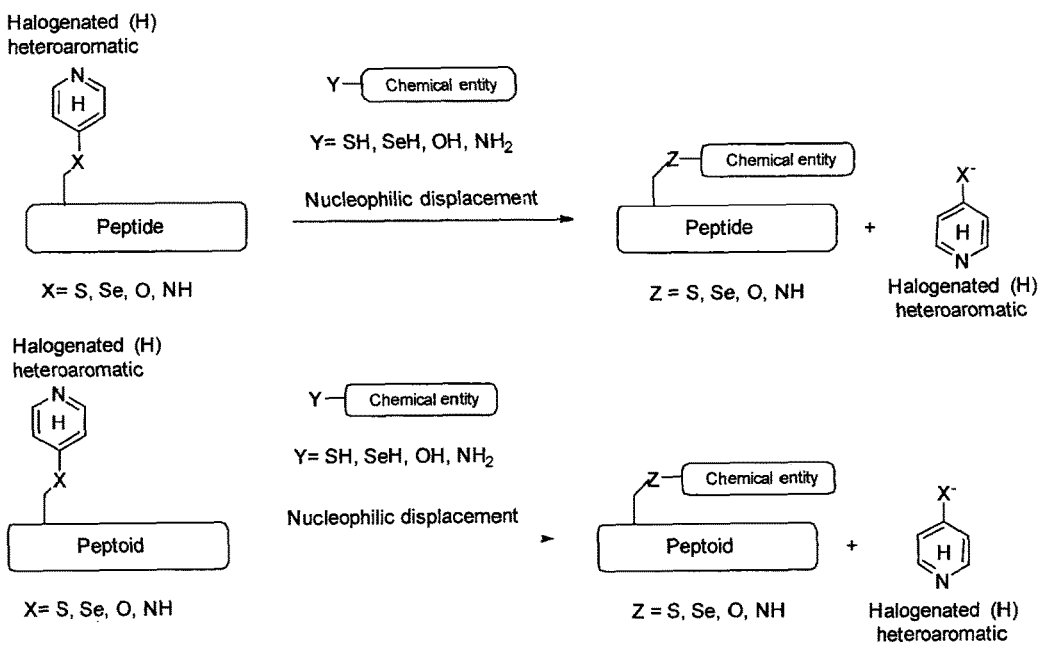
FIG. 2 is a schematic diagram showing the method developed for chemical modification of a protein or peptide according to the present invention.

The applicant has developed a new technology platform that allows chemical moieties to be attached to a peptide or protein in a manner that does not involve a linker. FIG. 2 is a schematic illustrating this embodiment of the present invention.

Figure 18:
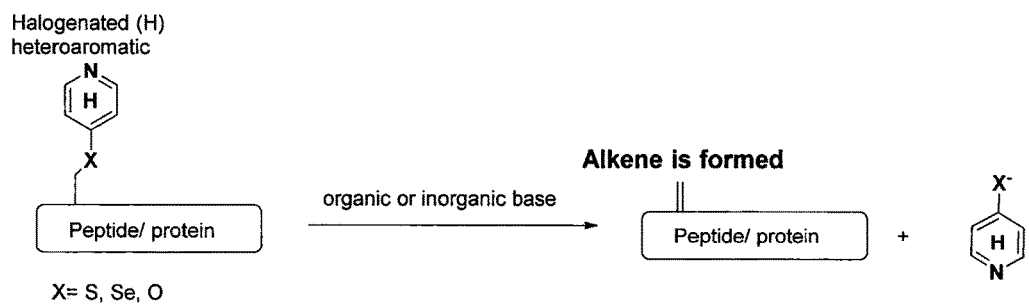
FIG. 18 is a schematic showing the method developed for accessing dehydroalanine containing peptides according to the present invention.

An alternative embodiment of the present invention allows the formation of dehydroalanine intermediates by a novel method. A schematic illustrating this embodiment is shown in FIG. 18.

Figure 19:
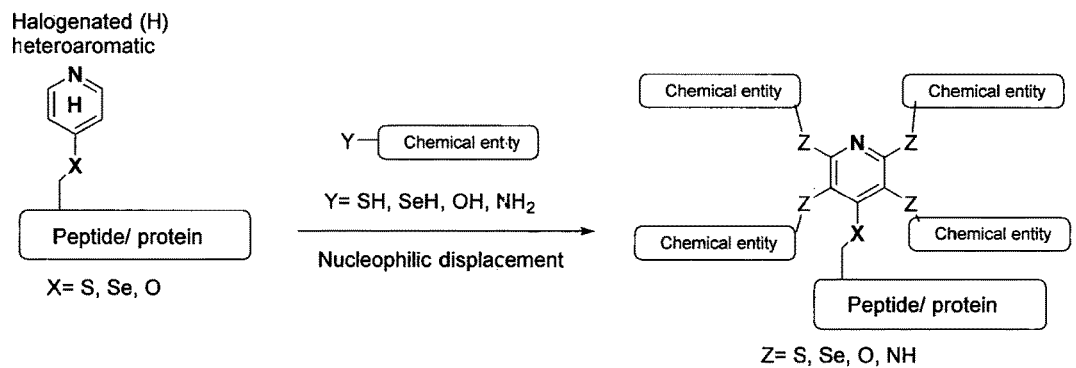
FIG. 19 is a schematic showing the method developed for accessing multiply chemically tagged peptides according to the present invention.

The applicant has also developed a new technology platform that allows multiple chemical moieties to be attached to a peptide or protein. FIG. 19 is a schematic illustrating this embodiment of the present invention.

Materials and Methods

Five different peptides, referred to as peptides 1 to 4, were prepared where:

Peptide 1 has the structure AcNH-Y-C-G-G-G-C-A-L-CONH$_2$;

Peptide 2 has the structure AcNH-A-C-Y-G-S-I-L-A-R-T-CONH$_2$;

Peptide 3 has the structure AcNH-F-C-G-G-G-C-A-L-CONH$_2$; and

Peptide 4 has the structure AcNH-F-S-G-G-G-S-A-L-CONH$_2$;

Peptides 1-4 was prepared using automated Fmoc-SPPS methods on a Liberty 1 peptide synthesizer (CEM) with microwave-assisted couplings (single coupling per amino acid; 10 min, 75° C. (50° C. for Fmoc-cys(trt)-OH coupling). Solid phase synthesis was conducted using Rink amide resin (0.7 mol/g loading) on a 0.1 mol scale, employing PyBOP and DIPEA as activator and base, respectively. Following on-resin synthesis of the appropriate sequence, N-terminal capping was achieved using Ac$_2$O/DMF (20%, 2×15 min) with shaking at room temperature. Finally, peptides were cleaved from the resin as the C-terminal amide by treatment of beads with a cleavage cocktail containing 90% TFA, 5% TIPS and 5% water with shaking at room temperature for 4 h. After removal of volatiles in vacuo, the product was triturated and washed using Et$_2$O.

Figure 15:
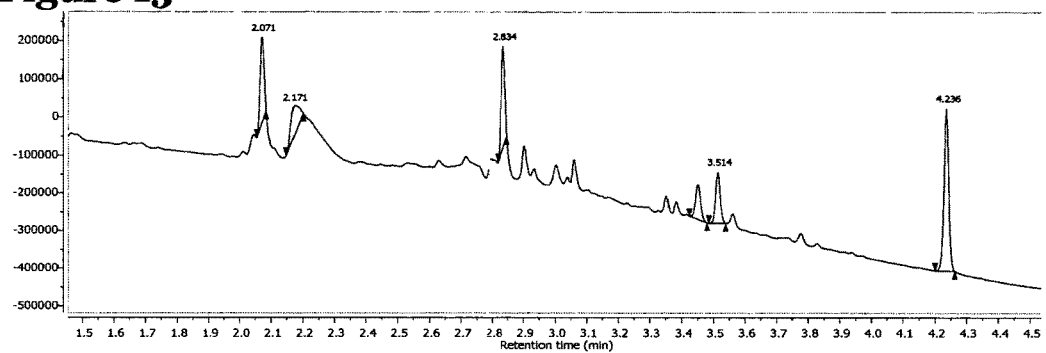
FIG. 15 is the LCMS spectrum for the crude reaction mixture resulting from the reaction shown in FIG. 17.

The structures of the fluoro-heteroaromatics and fluoro-aromatic used are shown in FIG. 15.

The peptides were reacted according to procedures A and B as described below:

Procedure A

Solid peptide (approx. 2 mg, 2.5 µmol) was dissolved in DMF (0.5 mL) in a 1.5 mL plastic Eppendorf tube, to which DIPEA (50 mM in DMF, 0.5 mL) was added. The fluoro-heteroaromatic or fluoroaromatic was then added in 25 equivalents and the tube was shaken at room temperature for 4.5 h. After removal of volatiles under vacuum, each reaction mixture was re-dissolved in a 1:1 mixture of H$_2$O and MeCN (1 mL) and analyzed by LCMS (ESI+).

Procedure B

Solid peptide (approx. 2 mg, 2.5 µmol) was dissolved in TFE (0.5 mL) in a 1.5 mL plastic Eppendorf tube, to which DIPEA (50 mM in TFE, 0.5 mL) was added. The fluoro-heteroaromatic or fluoroaromatic was added in 25 equivalents and the tube was shaken at room temperature for 4.5 h. After removal of volatiles under vacuum, each reaction mixture was re-dissolved in a 1:1 mixture of H$_2$O and MeCN (1 mL) and analyzed by LCMS (ESI+) and $^{19}$F NMR (100 µL D$_2$O added).

Procedure C

DIPEA (20 µL) was added to a solution of peptide (0.3 mg) in MeCN (0.5 mL) and water (0.5 mL) in a 1.5 mL plastic Eppendorf tube. A sulphur nucleophile was added in 5 equivalents and the tube was shaken at room temperature for 4 h and then analyzed by LCMS (ESI+).

The inventor has found that when the reagents are reacted according to procedure B the fluoro-heteroaromatic selectively reacts with cysteine residues instead of the tyrosine residues.

LC-MS Conditions:

Peptides and peptoids were characterised by LC-MS, ESI-LC MeCN (TQD mass spectrometer and an Acquity UPLC from Waters) using an Acquity UPLC BEH C8 1.7 µm (2.1 mm×50 mm) column and (C18 as of Jun. 2, 2015 3 pm) with a flow rate of 0.6 ml min$^{-1}$, a linear gradient of 5-95% of solvent B over 3.8 min (A=0.1% formic acid in H$_2$O, B=0.1% formic acid in MeCN) and injection volume of 1 µl.

QToF (mass spectrometer and an Acquity UPLC from Waters) using an Acquity UPLC BEH C8 1.7 µm (2.1 mm×50 mm) column with a flow rate of 0.6 ml min$^{-1}$, a linear gradient of 0-99% of solvent B over 5 min (A=0.1% formic acid in H$_2$O, B=0.1% formic acid in MeCN) and injection volume of 3 µl.

Peptides and peptoids identities were also confirmed by MALDI-TOF mass spectra analysis (Autoflex II ToF/ToF mass spectrometer Bruker Daltonik GmBH) operating in positive ion mode using an α-cyano-4-hydroxycinnamic acid (CHCA or CHHA) matrix. Data processing was done with MestReNova Version 10.0.

TQD

ESI-LC MeCN (TQD): Acquity UPLC BEH C8 1.7 µm (2.1 mm×50 mm) (C18 as of Jun. 2, 2015 3 pm)

Mobile phase: water containing formic acid (0.1% v/v): Acetonitrile

Flow rate 0.6 ml min$^{-1}$

Injection volume: 1 µl

Gradient:

| Time (min) | % A | % B |
|---|---|---|
| 0 | 95 | 5 |
| 0.2 | 95 | 5 |
| 4 | 5 | 95 |
| 4.5 | 5 | 95 |
| 5 | 95 | 5 |

Data processing: MestReNova 10.0

QToF

Accurate mass: Acquity UPLC BEH C18 1.7 µm (2.1 mm×100 mm)

Mobile phase: water containing formic acid (0.1% v/v): Acetonitrile

Flow rate: 0.6 ml min$^{-1}$

Injection volume: 3 µl

Gradient:

| Time (min) | % A | % B |
|---|---|---|
| 0 | 100 | 0 |
| 5 | 1 | 99 |
| 6 | 1 | 99 |
| 6.1 | 100 | 0 |
| 7 | 100 | 0 |

Data processing: MestReNova 10.0

MALDI

Autoflex II ToF/ToF mass spectrometer Bruker Daltonik GmBH 337 nm nitrogen laser Sample preparation 1 mg/ml, 1 µl spotted on matrix Operating in positive ion mode using an α-cyano-4-hydroxycinnamic acid (CHCA or HCCA) matrix Data acquisition: reflecton mode of analysis Data processing: MestReNova 10.0

EXAMPLE 1

Reacting Peptides 1 to 4 with Fluoro-Heteroaromatic or Fluoroaromatic Compounds to Obtain Activated Peptides Peptides 1 to 4 were further reacted using either procedure A or procedure B to create a stock of modified peptides, as set out in table 1.

TABLE 1

Reaction of peptides 1 to 4 according to procedure A or B

| Peptide | Fluoro-heteroaromatic | LCMS spectrum and chromatogram | Product |
| --- | --- | --- | --- |
| 1* | 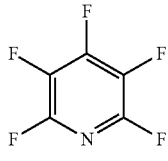<br>IX | One major peak in the LCMS chromatogram with a retention time of 2.617 minutes, the spectrum for the peark shows an [M + H]⁺ at 1081.629 m/z. | 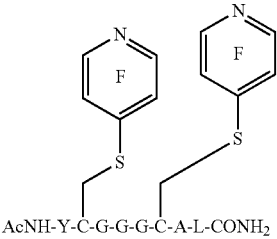<br>AcNH-Y-C-G-G-G-C-A-L-CONH$_2$<br>Peptide 5 |
| 2 | 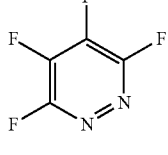<br>I | One major peak in the LCMS chromatogram with a retention time of 3.242 minutes, the spectrum for this peak shows an [M + H]⁺ peak at 1603 m/z. | 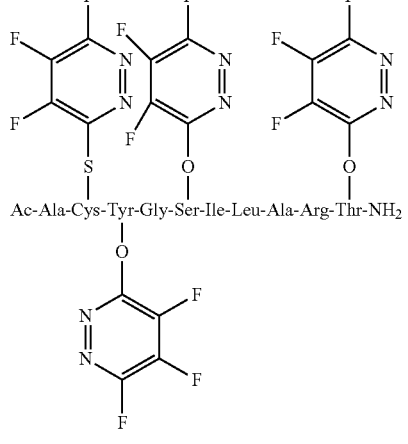<br>Ac-Ala-Cys-Tyr-Gly-Ser-Ile-Leu-Ala-Arg-Thr-NH$_2$<br>Peptide 6 |

TABLE 1-continued

Reaction of peptides 1 to 4 according to procedure A or B

| Peptide | Fluoro-heteroaromatic | LCMS spectrum and chromatogram | Product |
|---|---|---|---|
| 2 | 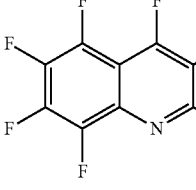<br>III | A peak in the LCMS chromatogram with retention times of 3.650 minutes. The spectrum for this peaks show an [M + H]+ peak at 1802 m/z.. | 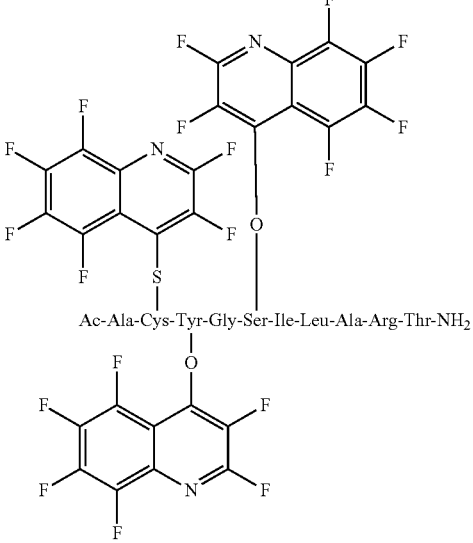<br>Peptide 7 |
| 2 | 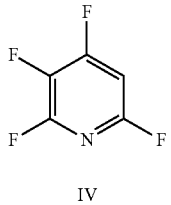<br>IV | One major peak in the LCMS chromatogram with a retention time of 2.683 minutes, the spectrum for this peak shows an [M + H]+ peak at 1357 m/z.. | 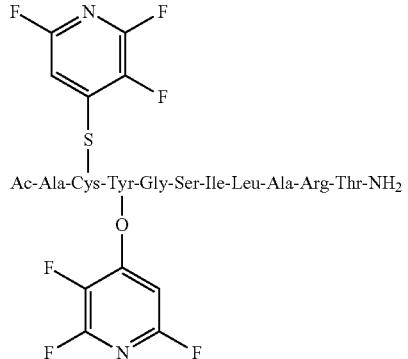<br>Peptide 8 |

TABLE 1-continued

Reaction of peptides 1 to 4 according to procedure A or B

| Peptide | Fluoro-heteroaromatic | LCMS spectrum and chromatogram | Product |
|---|---|---|---|
| 2 | 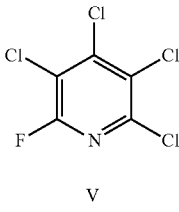<br>V | One major peak in the LCMS chromatogram with a retenetion time of 4.067 minutes, the spectrum for this peak shows an [M + H]⁺ peak at 1740 m/z. | 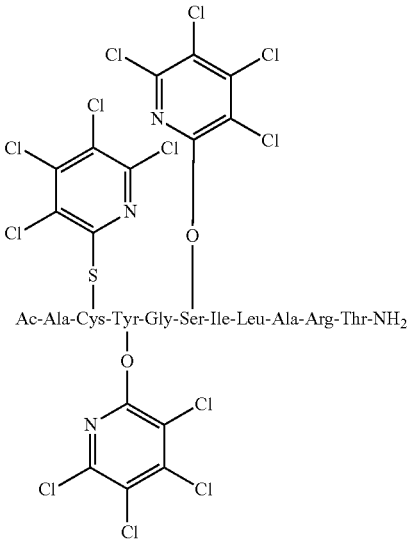<br>Peptide 9 |
| 2 | 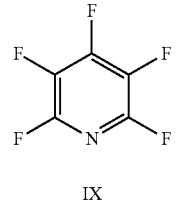<br>IX | One major peak in the LCMS chromatogram with a retention time of 3.458 minutes, the spectrum for this peak shows an [M + H]⁺ peak at 1691 m/z. | 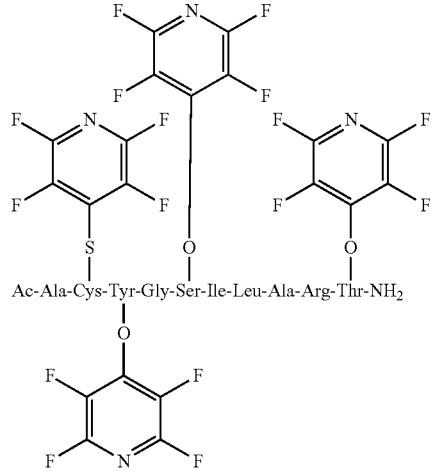<br>Peptide 10 |
| 2 | 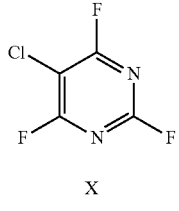<br>X | Two major peaks in the LCMS chromatogram with retention times of 2.750 minutes and 3.833 minutes. The spectrum for these peaks show an [M + 2MeCN + H]⁺ peak at 1288 m/z and an [M + H]+ peak at 1686 m/z. | 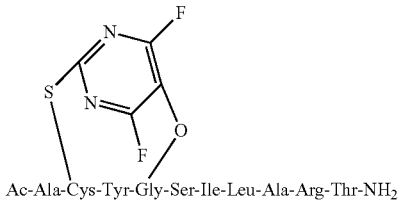<br>Peptide 11a and |

TABLE 1-continued

Reaction of peptides 1 to 4 according to procedure A or B

| Peptide | Fluoro-heteroaromatic | LCMS spectrum and chromatogram | Product |
|---|---|---|---|
| | | | 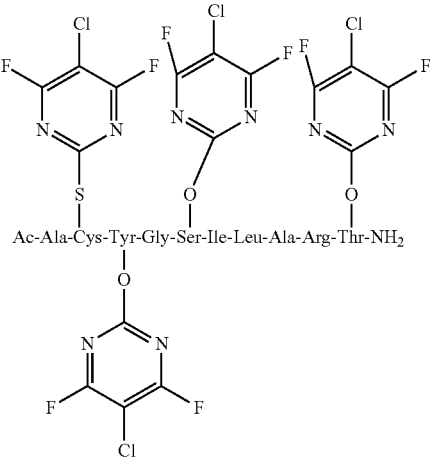<br>Peptide 11b |
| 3 | 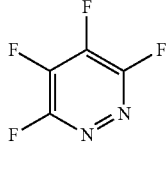<br>I | One major peak in the LCMS chromatogram with a retention time of 2.292 minutes, the spectrum for this peak shows an [M + H]$^+$ peak at 880 m/z. | 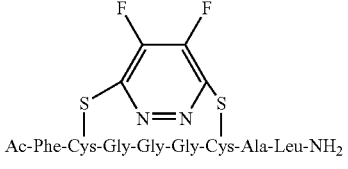<br>Peptide 12 |
| 3 | 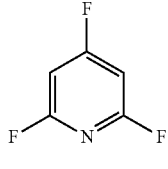<br>II | One major peak in the LCMS chromatogram with a retention time of 2.942 minutes, the spectrum for this peak shows an [M + H]$^+$ peak at 994 m/z. | 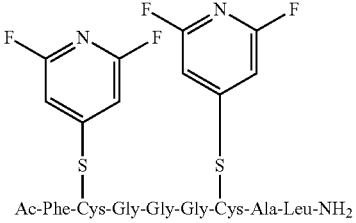<br>Peptide 13 |

TABLE 1-continued

Reaction of peptides 1 to 4 according to procedure A or B

| Peptide | Fluoro-heteroaromatic | LCMS spectrum and chromatogram | Product |
|---|---|---|---|
| 3 | 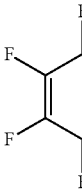<br>III | Two major peaks in the LCMS chromatogram with retention times of 3.650 minutes and 3.883 minutes. The spectrum for these peaks show an [M + H]$^+$ peak at 1238 m/z and an [M + H]$^+$ peak at 982 m/z. | 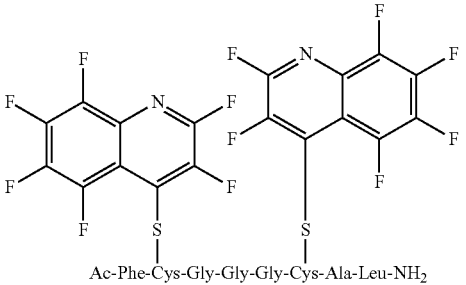<br>Peptide 14a and<br>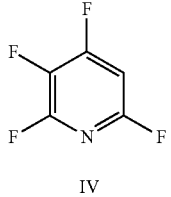<br>Peptide 14b |
| 3 | 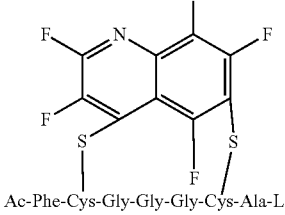<br>IV | Major peak in the LCMS chromatogram with a retention time of 3.083 minutes. The spectrum for this peak shows an [M + H]$^+$ peak at 1030 m/z. | 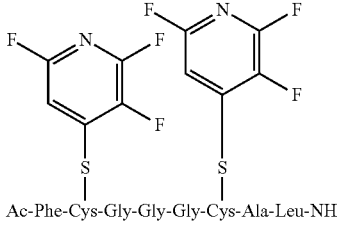<br>Peptide 15 |

TABLE 1-continued

Reaction of peptides 1 to 4 according to procedure A or B

| Peptide | Fluoro-heteroaromatic | LCMS spectrum and chromatogram | Product |
|---|---|---|---|
| 3 | 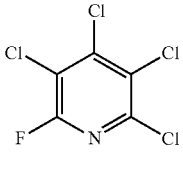<br>V | Two major peaks in the LCMS chromatogram with retention times of 4.058 minutes and 4.300 minutes. The spectrum for these peaks show an [M + H]⁺ peak at 1181 m/z and an [M + H]⁺ peak at 1189 m/z. | 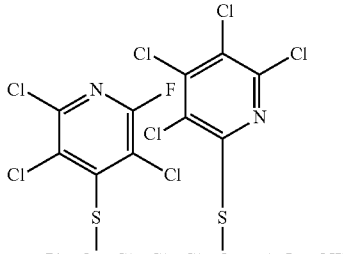<br>Peptide 16a; and<br>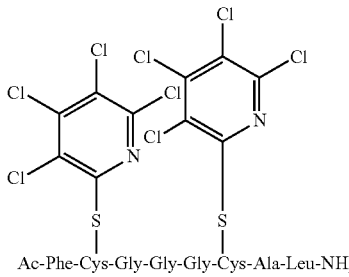<br>Peptide 16b |
| 3 | 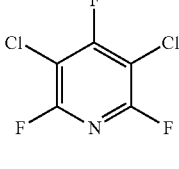<br>VI | Two major peaks in the LCMS chromatogram with retention times of 3.558 minutes and 2.583 minutes. The spectrum for these peaks showed [M + H]⁺ peaks at 1132 m/z, 929 m/z. | 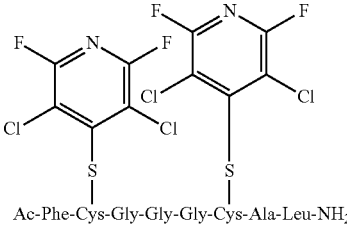<br>Peptide 17a; and<br>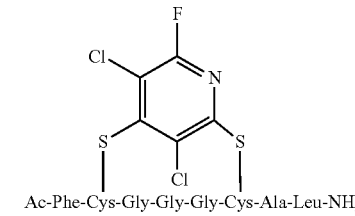<br>Peptide 17b |

TABLE 1-continued

Reaction of peptides 1 to 4 according to procedure A or B

| Peptide | Fluoro-heteroaromatic | LCMS spectrum and chromatogram | Product |
|---|---|---|---|
| 34 | VII | One major peak in the LCMS chromatogram with a retention time of 3.275 minutes, the spectrum for this peak shows [M + H]⁺ peaks at 1169 m/z and 1155 m/z. | Ac-Phe-Cys-Gly-Gly-Gly-Cys-Ala-Leu-NH₂<br><br>Peptide 18a; and<br><br>Ac-Phe-Cys-Gly-Gly-Gly-Cys-Ala-Leu-NH₂<br><br>Peptide 18b |
| 3 | VIII | Two major peaks in the LCMS chromatogram with retention times of 3.458 minutes and 2.758 minutes. The spectrum for these peaks show an [M + H]⁺ peak at 1100 m/z and an [M + H]+ peak at 914 m/z. | Ac-Phe-Cys-Gly-Gly-Gly-Cys-Ala-Leu-NH₂<br><br>Peptide 19a; and<br><br>Ac-Phe-Cys-Gly-Gly-Gly-Cys-Ala-Leu-NH₂<br><br>Peptide 19b |
| 3 | IX | One major peak in the LCMS chromatogram with retention times of 3.458 minutes. and 2.958 minutes. The spectrum for this peak show an [M + H]⁺ peak at 1066 m/z. | Ac-Phe-Cys-Gly-Gly-Gly-Cys-Ala-Leu-NH₂<br><br>Peptide 20 |

TABLE 1-continued

Reaction of peptides 1 to 4 according to procedure A or B

| Peptide | Fluoro-heteroaromatic | LCMS spectrum and chromatogram | Product |
|---------|----------------------|--------------------------------|---------|
| 3 | X (5-chloro-2,4,6-trifluoropyrimidine) | Two major peaks in the LCMS chromatogram with retention times of 3.208 minutes and 2.417 minutes. The spectrum for these peaks show [M + H]+ peaks at 1064 m/z, 896 m/z and 879 m/z. | Peptide 21a; Peptide 21b; and Peptide 21c (Ac-Phe-Cys-Gly-Gly-Gly-Cys-Ala-Leu-NH$_2$) |
| 4 | I (3,4,5,6-tetrafluoropyridazine) | Two major peaks in the LCMS chromatogram with retention times of 2.125 minutes and 2.197 minutes. The spectrum for these peaks show [M + H]+ peaks at 868 m/z, 1000 m/z and 848 m/z. | Peptide 22a; Peptide 22b; and Peptide 22c (Ac-Phe-Ser-Gly-Gly-Gly-Ser-Ala-Leu-NH$_2$) |

TABLE 1-continued

Reaction of peptides 1 to 4 according to procedure A or B

| Peptide | Fluoro-heteroaromatic | LCMS spectrum and chromatogram | Product |
|---|---|---|---|
| 4 | 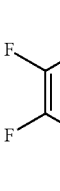<br>III | Two major peaks in the LCMS chromatogram with retention times of 3.650 minutes and 2.708 minutes. The spectrum for these peaks show [M + H]⁺ peaks at 1206 m/z and 951 m/z. | 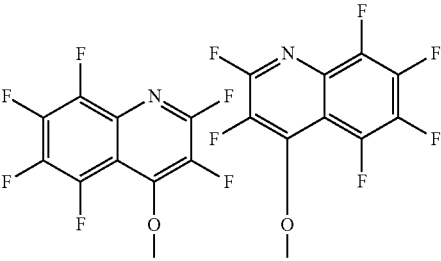<br>Peptide 23a; and<br><br>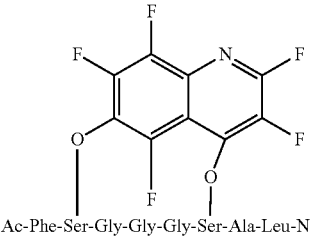<br>Peptide 23b |
| 4 | 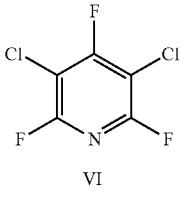<br>VI | One major peak in the LCMS chromatogram with a retention time of 3.558 minutes, the spectrum for this peak shows an [M + H]⁺ peak at 1100 m/z. | 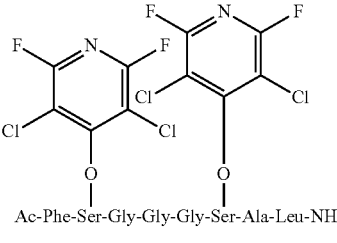<br>Peptide 24 |
| 4 | 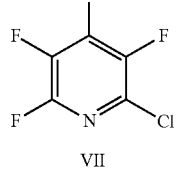<br>VII | One major peak in the LCMS chromatogram with a retention time of 3.275 minutes, the spectrum for this peak shows an [M + H]⁺ peak at 1066 m/z. | 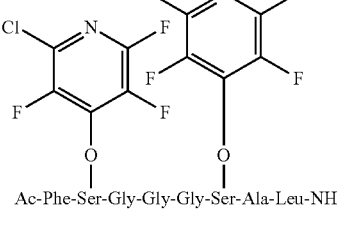<br>Peptide 25 |
| 4 | 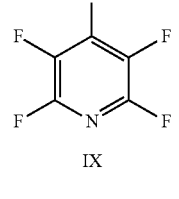<br>IX | One major peak in the LCMS chromatogram with retention times of 3.467 minutes. The spectrum for this peak show an [M + H]⁺ peak at 1140 m/z. | 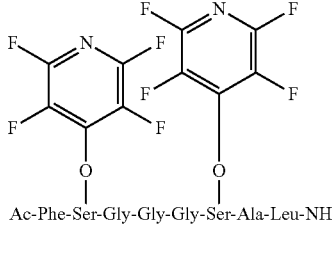<br>Peptide 26 |

TABLE 1-continued

Reaction of peptides 1 to 4 according to procedure A or B

| Peptide | Fluoro-heteroaromatic | LCMS spectrum and chromatogram | Product |
|---|---|---|---|
| 4 | 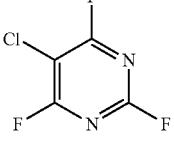 X | Two major peaks in the LCMS chromatogram with retention times of 2.133 minutes and 3.025 minutes. The spectrum for these peaks show [M + H]+ peaks at 884 m/z and 1032 m/z. | 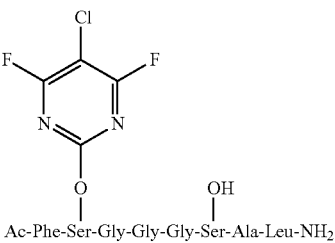  Ac-Phe-Ser-Gly-Gly-Gly-Ser-Ala-Leu-NH₂<br>Peptide 27a; and<br>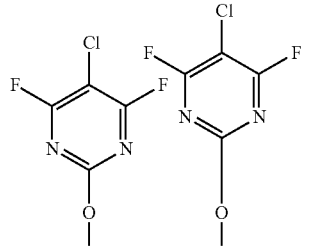  Ac-Phe-Ser-Gly-Gly-Gly-Ser-Ala-Leu-NH₂<br>Peptide 27b |

*The reaction for this entry was carried out using procedure B. All other reactions were performed using procedure A.

It will be readily appreciated that while a selection of fluoro-heteroaromatic compounds were used in this instance many more fluoro-heteroaromatic compounds could be used to create a peptide with a suitable leaving group. FIG. 10 shows the structures of some suitable fluoro-heteroaromatic compounds. Alternatively, it will be appreciated that further fluoro-heteroaromatic compound could be used, such as fused six-membered rings.

EXAMPLE 2

Reaction of Peptide 6 with Thiophenolate

Peptide 6 was reacted with thiophenolate according to the following reaction procedure:

To a solution of Peptide 6 (2 mg, 1.8 μmol) in MeCN (0.5 mL) and water (0.5 mL) in a 1.5 mL plastic Eppendorf tube, was added DIPEA (20 μL). Sodium thiophenolate was added in 5 equivalents and the tube was shaken at room temperature for 4 h and then analyzed by LCMS (ESI+).

Figure 13:
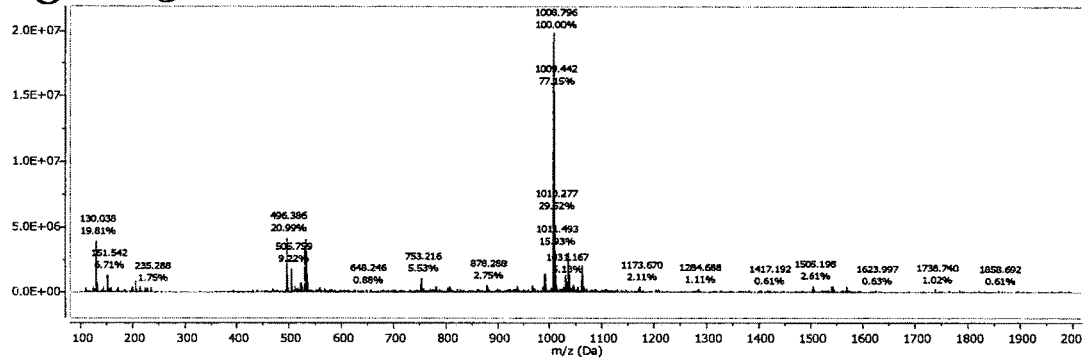
FIG. 13 is the mass spectrometry (MS) data from the peak at 2.508 minutes in the LCMS spectrum of FIG. 13.

An LCMS spectrum of the crude reaction mixture is shown in FIG. 12, and MS data from the peak at 2.508 minutes is shown in FIG. 13. Analysis of the crude reaction mixture suggested that the thio-fluoroheteroaryl group was substituted by the thiophenolate. The peak at 1008.796 m/z in FIG. 13 corresponds to an [M+H]+ peak for a single thiophenolate substituted product.

FIG. 11 shows the reaction which occurred.

Accordingly, one embodiment of the present invention is a method for attaching a chemical moiety to a peptide or protein in a manner that does not involve a linker.

EXAMPLE 3

Reaction of Peptide 6 with Thioacetate

Peptide 6 was reacted with potassium thioacetate according to the following reaction procedure:

To a solution of Peptide 6 (2 mg, 1.8 μmol) in MeCN (0.5 mL) and water (0.5 mL) in a 1.5 mL plastic Eppendorf tube, was added DIPEA (20 μL). Potassium thioacetate was added in 5 equivalents and the tube was shaken at room temperature for 4 h and then analyzed by LCMS (ESI+).

Figure 16:
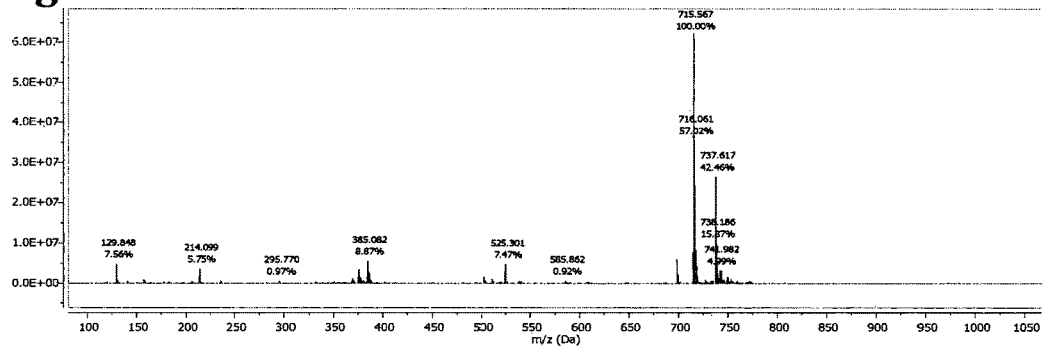
FIG. 16 is the mass spectrometry (MS) data from the peak at 2.071 minutes in the LCMS spectrum of FIG. 18.
Figure 17:
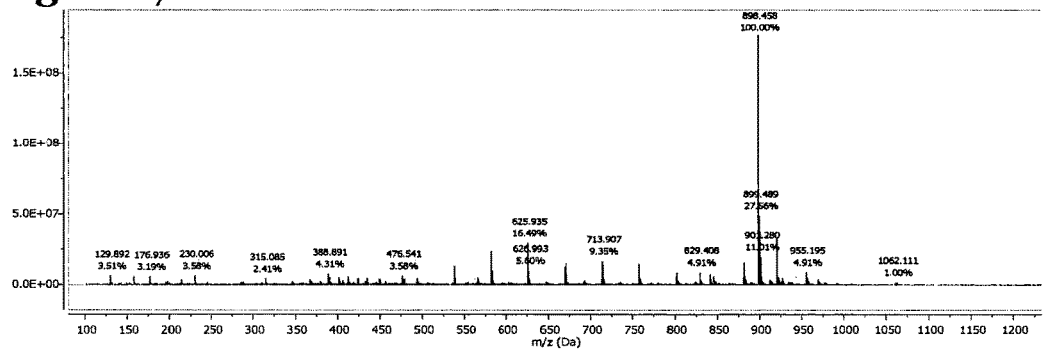
FIG. 17 is the mass spectrometry (MS) data from the peak at 2.834 minutes in the LCMS spectrum of FIG. 18.

An LCMS spectrum of the crude reaction mixture is shown in FIG. 15, and MS data from the peaks at 2.071 minutes and 2.834 minutes is shown in FIGS. 16 and 17 respectively. Analysis of the crude reaction mixture suggested that the thio-fluoroheteroaryl group was eliminated to afford the dehydroalanine. The peak at 715.567 m/z in FIG. 17 corresponds to an [M+H]+ peak for the mono-eliminated product and the peak at 898.458 m/z in FIG. 20 corresponds to an [M+H]+ peak for the di-eliminated product.

Figure 14:
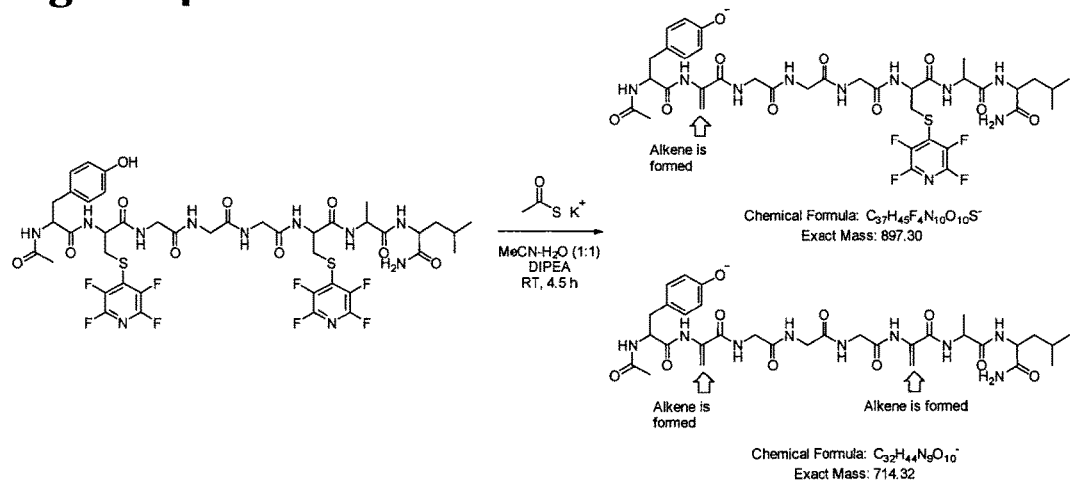
FIG. 14 shows the reaction of a fluoro-pyridine activated peptide with thioacetate.

FIG. 14 shows the reaction which occurred.

Accordingly, an alternative embodiment of the present invention is a new method enabling the creation of dehydroalanine containing peptides. The general approach for this is shown in FIG. 18. Dehydroalanine containing peptides can be used as reactive intermediates in the formation of bioconjugates, as demonstrated by the work carried out by the Davis group. For instance, dehydroalanine containing peptides are well known to act as substrates for the addition of various sulphur nucleophiles.

EXAMPLE 4

Further Reaction of Activated Peptides with Sulphur Nucleophiles

The activated peptides obtained by reacting peptide 2 with various fluoroheteroaromatic compounds in Example 1 were further reacted with various sulphur nucleophiles according to Procedure C.

TABLE 2

Reaction of Peptides 6, 8, 9, 10, 11a and 11b with sulphur nucleophiles according to procedure C

| Peptide | Sulphur Nucleophile | Product |
|---|---|---|
| 6 | | |

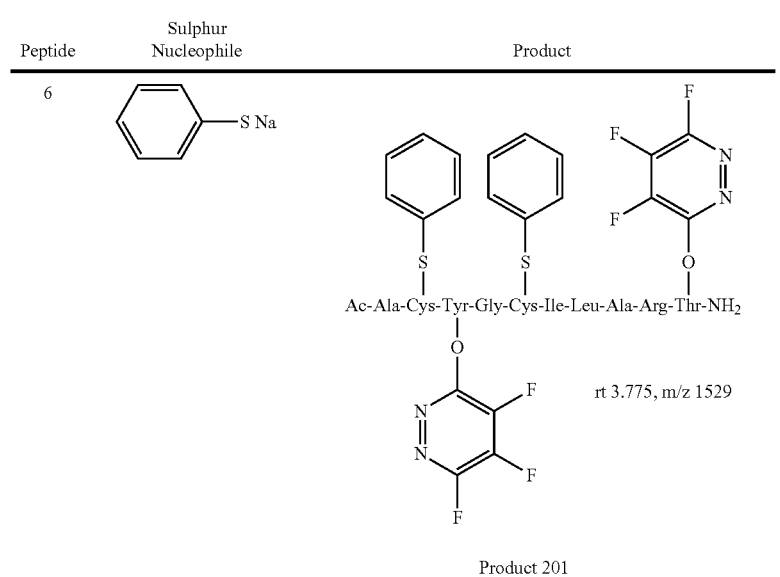

rt 3.775, m/z 1529

Product 201

| 8 | | |

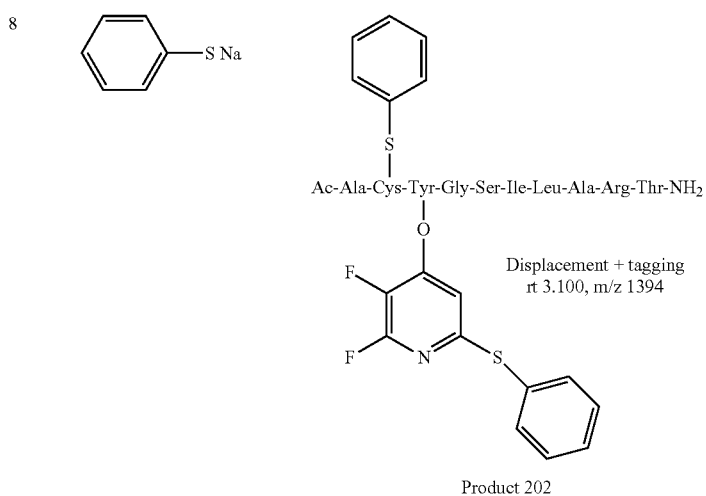

Displacement + tagging
rt 3.100, m/z 1394

Product 202

TABLE 2-continued
Reaction of Peptides 6, 8, 9, 10, 11a and 11b with sulphur nucleophiles according to procedure C
| Peptide | Sulphur Nucleophile | Product |
|---|---|---|
| | | Product 203, Tagging rt 3.100, m/z 1447 |
| 9 | 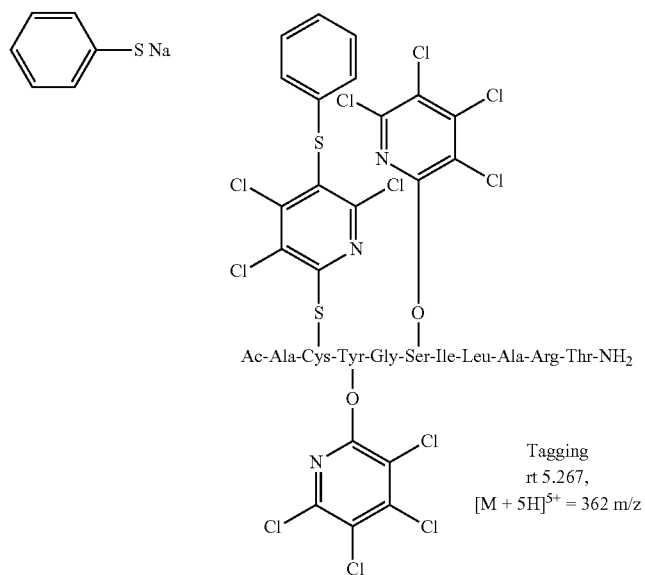 | Product 204, Tagging rt 5.267, $[M + 5H]^{5+} = 362$ m/z |

TABLE 2-continued
Reaction of Peptides 6, 8, 9, 10, 11a and 11b with sulphur nucleophiles according to procedure C
| Peptide | Sulphur Nucleophile | Product |
|---|---|---|
| 9 | | 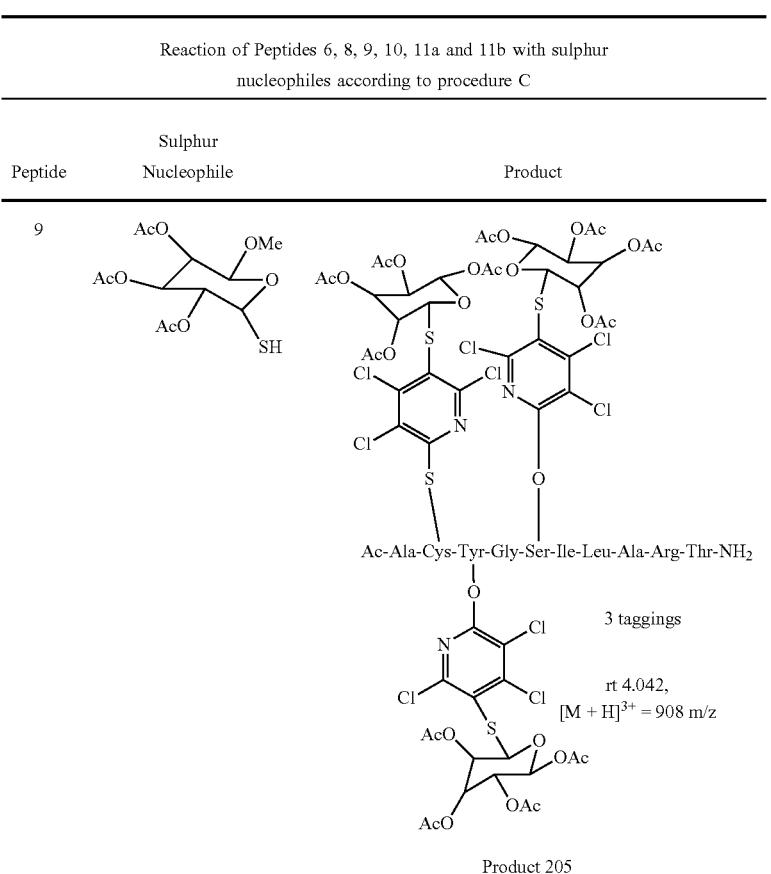 3 taggings<br>rt 4.042,<br>$[M + H]^{3+}$ = 908 m/z<br><br>Product 205 |
| 10 | | 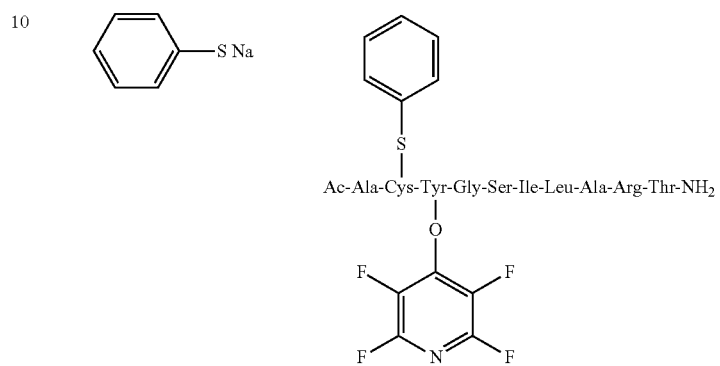 Single tagging + Ser and Thr hydrolisis<br>rt 3.100, m/z 1323<br><br>Ptoduct 206 |

TABLE 2-continued
Reaction of Peptides 6, 8, 9, 10, 11a and 11b with sulphur nucleophiles according to procedure C
| Peptide | Sulphur Nucleophile | Product |
| --- | --- | --- |
| 11a and 11b | | |
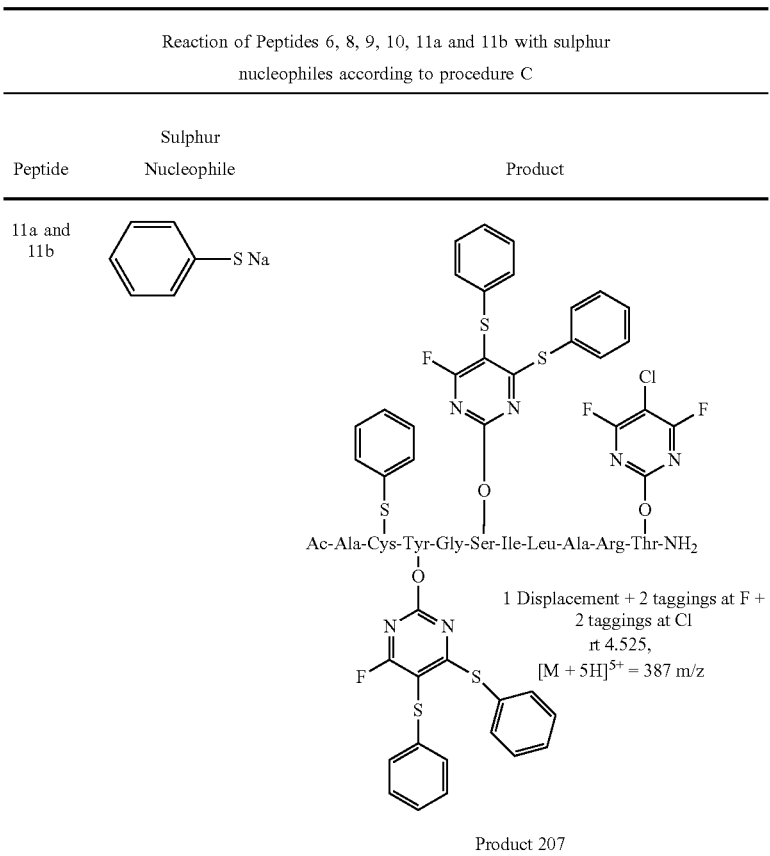
Product 207
| 11a and 11b | | |
| --- | --- | --- |
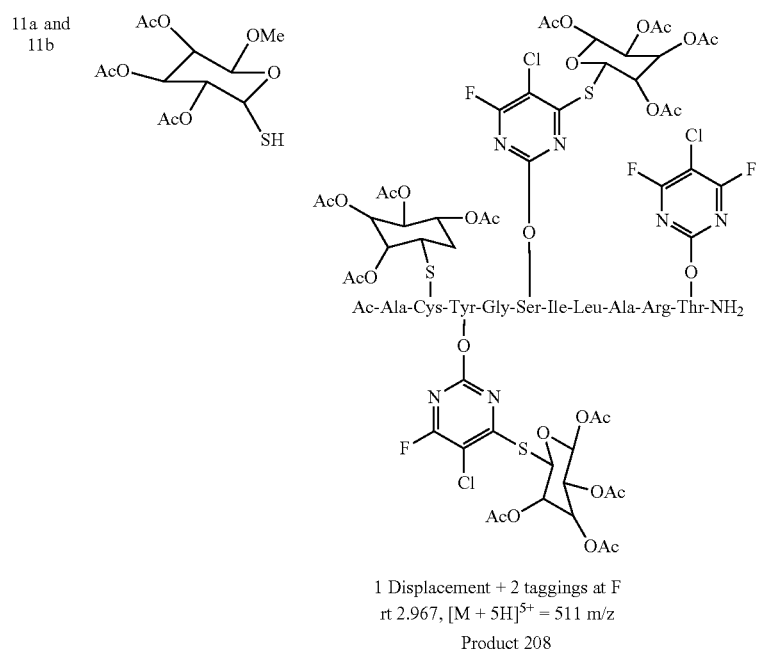
Product 208

When peptide 6 was exposed to sodium thiophenolate, the sulphur nucleophile displaced two heteroaromatic groups on peptide 6 to give product 201. This results in original peptide 2 having been tagged, without using a linker, at a cysteine residue and a serine residue.

Similarly, when peptides 8, 10 and 11a were reacted with sodium thiophenolate peptide 8 reacted to give product 202, peptide lo reacted to give product 206, and peptide 11a reacted to give product 207, all of which have undergone a displacement reaction. This results in original peptide 2 having been tagged, without using a linker, at a cysteine residue.

For the aforementioned reactions the peptides underwent displacement reactions but the heteroaromatic group attached on the tyrosine resides were unreacted. Accordingly, the inventors have shown that it is possible to selectively tag molecules at chosen residues (i.e. cysteine or serine) in the presence of an activated tyrosine residue. Additionally, the inventors have shown that sometimes instead of displacing a heteroaromatic group the sulphur nucleophile instead displaces one or more of the halogens on the aromatic ring. Due to the presence of multiple halogens on the ring, it is possible to add multiple tags to a heteroaromatic group. An example of this is where peptide 11a reacted with sodium thiophenolate to give the product 207. An example of displacing only one halogen can be seen in the reaction between peptide 9 and the nucleophile 1-Thio-β-D-glucose tetraacetate which affords the product 205.

EXAMPLE 5

Further Reaction of Activated Peptides with Sulphur Nucleophiles

The activated peptides obtained by reacting peptide 3 with various fluoroheteroaromatic compounds in Example 1 were further reacted with various sulphur nucleophiles according to Procedure C.

TABLE 3

Reaction of Peptides 12 and 14b with sulphur nucleophiles according to procedure C

| Peptide(s) | Sulphur Nucleophile | Product |
|---|---|---|
| 12 | AcO, OMe, AcO, AcO, SH (sugar-SH) | Product 301: fluoro-pyridazine bridge bearing sugar-S and cyclic peptide S attachments, Ac-Phe-Cys-Gly-Gly-Gly-Cys-Ala-Leu-NH₂, rt 3.258, m/z 1224 |
| 14b | AcO, OMe, AcO, AcO, SH (sugar-SH) | Product 302: fluoro-quinoline bridge bearing sugar-S and cyclic peptide S attachments, Ac-Phe-Cys-Gly-Gly-Gly-Cys-Ala-Leu-NH₂, rt 3.158, m/z 1327 |

When peptide 12 was exposed to 1-thio-β-D-glucose tetraacetate, the sulphur nucleophile displaced one of the fluorine atoms on the fluoro-heteroaromatic bridge to give product 301. Similarly when peptide 14b was exposed to 1-thio-β-D-glucose tetraacetate, the sulphur nucleophile displaced on of the fluorine atoms on the fluoro-heteroaromatic bridge to give product 302. This demonstrates that it is possible to tag a fluoro-heteroaromatic containing cyclic peptides without causing degradation of the cyclic peptide. This approach offers a novel route to prepare tagged cyclic peptides.

It should be noted that when peptide 3 was modified using a hexafluorobenzene , to give peptide 19, the inventors found that this modified peptide did not react with the sulphur nucleophile to give a tagged cyclic product. This highlights the advantage over the prior art afforded through the application of a perfluoro-heteroaromatic reagent to activate the peptides.

EXAMPLE 6

Further Reaction of Activated Peptides with Sulphur Nucleophiles

The activated peptides obtained by reacting peptide 4 with various fluoroheteroaromatic compounds in Example 1 were further reacted with various sulphur nucleophiles according to Procedure C.

TABLE 4

Reaction of Peptides 22a, 22b, 23a and 27b with sulphur nucleophiles according to procedure C

| Peptide | Sulphur Nucleophile | Product |
|---|---|---|
| 22a and 22b | ![structure with AcO, OMe, SH] | ![product structure]<br>Ac-Phe-Ser-Gly-Gly-Gly-Ser-Ala-Leu-NH$_2$<br>1 tagging<br>rt 2.925, m/z 1213<br>Product 401 |

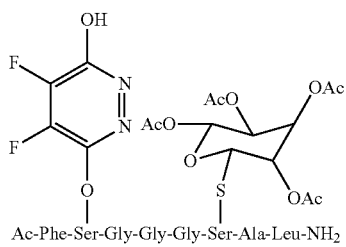

Ac-Phe-Ser-Gly-Gly-Gly-Ser-Ala-Leu-NH$_2$ rt 2.925, m/z 1213

Product 402

TABLE 4-continued
Reaction of Peptides 22a, 22b, 23a and 27b with sulphur nucleophiles according to procedure C
| Peptide | Sulphur Nucleophile | Product |
|---|---|---|
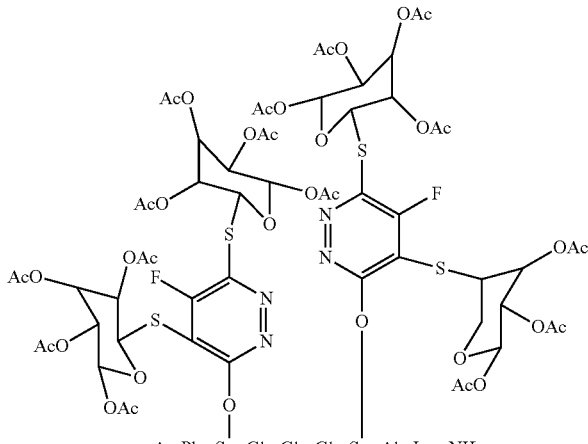
rt 3.792, $[M + H + Na]^{2+} = 1199$ m/z
Product 403
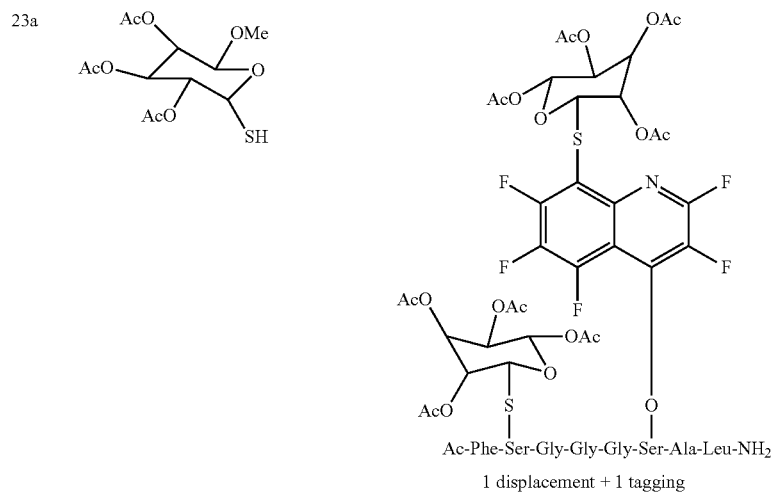
1 displacement + 1 tagging
rt 4.017, m/z 1341
Product 405

TABLE 4-continued

Reaction of Peptides 22a, 22b, 23a and 27b with sulphur nucleophiles according to procedure C

| Peptide | Sulphur Nucleophile | Product |
|---------|---------------------|---------|
| 27b | Ph-S Na | [structure] Ac-Phe-Ser-Gly-Gly-Gly-Ser-Ala-Leu-NH$_2$ 5 tagging rt 4.525, [M + 5H]$^{5+}$ = 301 m/z Product 406 |

When peptide 22b was exposed to 1-thio-β-D-glucose tetraacetate, the sulphur nucleophile displaced one heteroaromatic group on peptide 22b to give product 402. This results in original peptide 4 having been tagged, without using a linker, at a serine residue.

When peptide 23a was exposed to 1-thio-β-D-glucose tetraacetate, the sulphur nucleophile displaced one heteroaromatic group on peptide 23a to give product 405. This results in original peptide 4 having been tagged, without using a linker, at a serine residue.

Additionally peptide 22ba reacted with 1-thio-β-D-glucose tetraacetate to give the product 403, where the sulphur nucleophile displaced two halogens on each aromatic ring, thereby adding multiple tags to the heteroaromatic group. Further examples of this include where peptide 23a reacted with sodium thiophenolate to give the multiply tagged product 404 and where peptide 27b reacted with sodium thiophenolate to give the multiply tagged product 406.

SUMMARY

Advantages of the invention include the possibility of chemically modifying activated peptides under mild conditions in a traceless fashion. Traceless chemical modification is not currently available through other published methodologies most of which require the use of a linker moiety being present in the final product. The methodology requires peptide activation via reaction with a halogenated heteroaromatic followed by nucleophilic displacement of the halogenated heteroaromatic. Selectivity between serine/cysteine activated residues and tyrosine activated residues has been demonstrated. Nucleophilic displacement occurs directly without the need to install a dehydro-alanine type motif which in other published methodologies leads to the loss of stereo-chemical integrity.

However, if the installation of a dehydro-alanine type motif is desired, the activated peptide can be reacted under mild conditions to install the motif into the peptide backbone.

Activation of a peptide through a halogenated heteroaromatic has also been shown to offer a route to attach multiple chemical moieties to a linear or cyclic peptide. The aforementioned reaction has been shown not to be possible if carried out with a published halogenated aromatic (e.g. hexafluorobenzene) activated peptide.

The invention claimed is:

1. A method for chemically modifying a peptide, derivative or analogue thereof, the method comprising:
   (i) contacting a peptide, derivative or analogue thereof comprising at least one nucleophilic side chain with a fluoro-heteroaromatic compound to activate the peptide, derivative or analogue thereof due to the formation of a leaving group on the peptide, derivative or analogue thereof, wherein the leaving group comprises the heteroaromatic compound, which is covalently bonded to the nucleophilic side chain, and at least a portion of the nucleophilic side chain; and
   (ii) contacting the activated peptide, derivative or analogue thereof with a nucleophile, wherein the nucleophile displaces the leaving group and creates a covalent bond between the peptide, derivative or analogue thereof and the nucleophile to create a chemically modified peptide, derivative or analogue thereof,
   wherein the derivative or analogue is:
   a) a peptide where one or more of the amino acids residues of the peptide are replaced by residues with similar side chains or peptide backbone properties;
   b) a peptide where terminal groups thereof are protected by N- and C-terminal protecting groups with similar properties to acetyl or amide groups;
   c) a peptoid;
   d) a retropeptoid;
   e) a peptide-peptoid hybrid; or
   f) a peptide where at least one of the amino acids residues of the peptide is a D-amino acid.

2. The method according to claim 1, wherein the fluoro-heteroaromatic compound contains at least one nitrogen atom in its aromatic ring.

3. The method according to claim 1, wherein the fluoro-heteroaromatic compound comprises at least one hydrogen atom, wherein each hydrogen atom is covalently bonded to a carbon atom in the aromatic ring, or the fluoro-heteroaromatic compound comprises a perfluoroaromatic compound, or the fluoro-heteroaromatic compound comprises a chloro-fluoro-heteroaromatic compound.

4. The method according to claim 1, wherein the nucleophilic side chain reacts in an SNAr type reaction with the fluoro-heteroaromatic compound to displace a fluorine atom and create a covalent bond between the nucleophilic side chain and the heteroaromatic compound.

5. The method according to claim 1, wherein step (i) of the method comprises dissolving a peptide, derivative or analogue thereof in a solvent, and adding a base thereto before the fluoro-heteroaromatic compound is added to the dissolved peptide to create a reaction solution.

6. The method according to claim 5, wherein the molar ratio of the peptide, derivative or analogue thereof to the fluoro-heteroaromatic compound in step (i) is between 1:1 and 1:100, or between 1:5 and 1:50, or between 1:10 and 1:40, or between 1:20 and 1:30 and/or the molar ratio of the activated peptide, derivative or analogue thereof to the nucleophile or base in step (ii) is between 1:1 and 1:100, or between 1:5 and 1:10, or between 1:10 and 1:40, or between 1:20 and 1:30.

7. The method according to claim 1, wherein the nucleophile:
   a) comprises an organic molecule possessing nucleophilic functionality; and/or
   b) includes at least one group possessing nucleophilic functionality which is selected from a thiol group, a hydroxyl group, a primary amine group, a secondary amine group and a selenol group; and/or c) is selected from the group consisting of: a thiol containing sugar, a thiol containing nucleoside, a thiol containing alkyl chain, a thiol containing PEGylating agent, a thiol containing fluorescent tag, a thiol containing antibody, a hydroxyl containing sugar, a hydroxyl containing nucleoside, a hydroxyl containing alkyl chain, a hydroxyl containing PEGylating agent, a hydroxyl containing fluorescent tag, a hydroxyl containing antibody, an amine containing sugar, an amine containing nucleoside, an amine containing alkyl chain, an amine containing PEGylating agent, an amine containing fluorescent tag, an amine containing antibody, a selenol group, a selenol containing sugar, a selenol containing nucleoside, a selenol containing alkyl chain, a selenol containing PEGylating agent, a selenol containing fluorescent tag and a selenol containing antibody; and/or d) is glutathione.

8. The method according to claim 1, wherein the chemical modification comprises conjugation of a chemical entity onto the peptide.

9. The method according to claim 1, wherein at least one of the nucleophilic side chains comprises an amine group.

10. The method according to claim 1, wherein at least one of the nucleophilic side chains comprises a thiol group.

11. The method according to claim 1, wherein at least one of the nucleophilic side chains comprises an alcohol group.

12. The method according to claim 1, wherein at least one of the nucleophilic side chains comprises a selenol group.

13. A chemically modified peptide, derivative or analogue thereof obtained by the method according to claim 1.

14. The chemically modified peptide, derivative or analogue thereof according to claim 13, wherein the chemically modified peptide, derivative or analogue thereof is functionalised or tagged with a selected chemical entity.

15. The method according to claim 2, wherein the fluoroheteroaromatic compound contains one, two or three nitrogen atoms in the aromatic ring.

16. The method according to claim 1, wherein the fluoroheteroaromatic compound contains at least one fluorine atom, where each fluorine atom is covalently bonded to a carbon atom in the aromatic ring.

17. The method according to claim 5, wherein the base is N,N-diisopropylethylamine (DIPEA).

18. The method according to claim 5, wherein the solvent is 2,2,2-trifluoroethanol (TFE).

19. The method according to claim 8, wherein the chemical entity is selected from the group consisting of a sugar, a thiosugar, a nucleoside, an alkyl chain, PEG, a fluorescent tag and an antibody.

20. The method according to claim 9, wherein the amine group is provided on an amino acid residue within the peptide, derivative or analogue thereof.

21. The method according to claim 9, wherein the amine group is provided on a lysine residue in the peptide, derivative or analogue thereof.

22. The method according to claim 10, wherein the thiol group is provided on a cysteine residue or modified cysteine residue in the peptide, derivative or analogue thereof.

23. The method according to claim 11, wherein the alcohol group comprises a phenol group.

24. The method according to claim 11, wherein the alcohol group is provided on a serine or threonine residue within the peptide, derivative or analogue thereof.

25. The method according to claim 12, wherein the selenol group is provided on a selenocysteine residue within the peptide, derivative or analogue thereof.

26. The chemically modified peptide, derivative or analogue thereof according to claim 14, wherein the chemical entity is selected from the group consisting of a sugar, a thiosugar, a nucleoside, an alkyl chain, PEG, a fluorescent tag and an antibody.

\* \* \* \* \*

SEQUENCE LISTING

<160> NUMBER OF SEQ ID NOS: 55

<210> SEQ ID NO 1
<211> LENGTH: 8
<212> TYPE: PRT
<213> ORGANISM: Artificial Sequence
<220> FEATURE:
<223> OTHER INFORMATION: Synthetic Sequence

```
<400> SEQUENCE: 1

Tyr Cys Gly Gly Gly Cys Ala Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 2

Ala Cys Tyr Gly Ser Ile Leu Ala Arg Thr
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 3

Phe Cys Gly Gly Gly Cys Ala Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 4

Phe Ser Gly Gly Gly Ser Ala Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      2,3,5,6-tetrafluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      2,3,5,6-tetrafluoro-pyridin-4-yl.

<400> SEQUENCE: 5

Tyr Xaa Gly Gly Gly Xaa Ala Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      3,4,5-trifluoro-pyridazin-6-yl.
```

```
<220> FEATURE:
<221> NAME/KEY: MOD_RES
<222> LOCATION: (3)..(3)
<223> OTHER INFORMATION: The Xaa is a Tyr residue substituted with
      3,4,5-trifluoro-pyridazin-6-yl.
<220> FEATURE:
<221> NAME/KEY: MOD_RES
<222> LOCATION: (5)..(5)
<223> OTHER INFORMATION: The Xaa is a Ser residue substituted with
      3,4,5-trifluoro-pyridazin-6-yl.
<220> FEATURE:
<221> NAME/KEY: MOD_RES
<222> LOCATION: (10)..(10)
<223> OTHER INFORMATION: The Xaa is a Thr residue is substituted with
      3,4,5-trifluoro-pyridazin-6-yl.

<400> SEQUENCE: 6

Ala Xaa Xaa Gly Xaa Ile Leu Ala Arg Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      perfluoroquinolin-4-yl.
<220> FEATURE:
<221> NAME/KEY: MOD_RES
<222> LOCATION: (3)..(3)
<223> OTHER INFORMATION: The Xaa is a Tyr residue substituted with
      perfluoroquinolin-4-yl.
<220> FEATURE:
<221> NAME/KEY: MOD_RES
<222> LOCATION: (5)..(5)
<223> OTHER INFORMATION: The Xaa is a Ser residue substituted with
      perfluoroquinolin-4-yl.

<400> SEQUENCE: 7

Ala Xaa Xaa Gly Xaa Ile Leu Ala Arg Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with a
      2,3,6-trifluoro-pyridin-4-yl.
<220> FEATURE:
<221> NAME/KEY: MOD_RES
<222> LOCATION: (3)..(3)
<223> OTHER INFORMATION: The Xaa is a Tyr residue substituted with a
      2,3,6-trifluoro-pyridin-4-yl.

<400> SEQUENCE: 8

Ala Xaa Xaa Gly Ser Ile Leu Ala Arg Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: MOD_RES
<222> LOCATION: (2)..(2)
<223> OTHER INFORMATION: The Xaa is a Cys residue substituted with a
      perchloropyridin-2-yl.
<220> FEATURE:
<221> NAME/KEY: MOD_RES
<222> LOCATION: (3)..(3)
<223> OTHER INFORMATION: The Xaa is a Tyr residue substituted with a
      perchloropyridin-2-yl.
<220> FEATURE:
<221> NAME/KEY: MOD_RES
<222> LOCATION: (5)..(5)
<223> OTHER INFORMATION: The Xaa is a Ser residue substituted with a
      perchloropyridin-2-yl.

<400> SEQUENCE: 9

Ala Xaa Xaa Gly Xaa Ile Leu Ala Arg Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      2,3,5,6-tetrafluoro-pyridin-4-yl.
<220> FEATURE:
<221> NAME/KEY: MOD_RES
<222> LOCATION: (3)..(3)
<223> OTHER INFORMATION: The Xaa is a Tyr residue substituted with
      2,3,5,6-tetrafluoro-pyridin-4-yl.
<220> FEATURE:
<221> NAME/KEY: MOD_RES
<222> LOCATION: (5)..(5)
<223> OTHER INFORMATION: The Xaa is a Ser residue substituted with
      2,3,5,6-tetrafluoro-pyridin-4-yl.
<220> FEATURE:
<221> NAME/KEY: MOD_RES
<222> LOCATION: (10)..(10)
<223> OTHER INFORMATION: The Xaa is a Thr residue substituted with
      2,3,5,6-tetrafluoro-pyridin-4-yl.

<400> SEQUENCE: 10

Ala Xaa Xaa Gly Xaa Ile Leu Ala Arg Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the Tyr
      residue.
<220> FEATURE:
<221> NAME/KEY: MOD_RES
<222> LOCATION: (3)..(3)
<223> OTHER INFORMATION: The Xaa is  Tyr residue cyclyated with the Cys
      residue.

<400> SEQUENCE: 11

Ala Xaa Xaa Gly Ser Ile Leu Ala Arg Thr
1               5                   10
```

```
<210> SEQ ID NO 12
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: Xaa is a Cys residue substituted with
      5-chloro-4,6-difluoro-pyrimidin-2-yl.
<220> FEATURE:
<221> NAME/KEY: MOD_RES
<222> LOCATION: (3)..(3)
<223> OTHER INFORMATION: The Xaa is a Tyr residue substituted with
      5-chloro-4,6-difluoro-pyrimidin-2-yl.
<220> FEATURE:
<221> NAME/KEY: MOD_RES
<222> LOCATION: (5)..(5)
<223> OTHER INFORMATION: The Xaa is a Ser residue substituted with
      5-chloro-4,6-difluoro-pyrimidin-2-yl.
<220> FEATURE:
<221> NAME/KEY: MOD_RES
<222> LOCATION: (10)..(10)
<223> OTHER INFORMATION: The Xaa is a Thr residue substituted with
      5-chloro-4,6-difluoro-pyrimidin-2-yl.

<400> SEQUENCE: 12

Ala Xaa Xaa Gly Xaa Ile Leu Ala Arg Xaa
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 13

Phe Xaa Gly Gly Gly Xaa Ala Leu
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      2,6-difluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      2,6-difluoro-pyridin-4-yl.

<400> SEQUENCE: 14

Phe Xaa Gly Gly Gly Xaa Ala Leu
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      perfluoroquinolin-4-yl.
<220> FEATURE:
<221> NAME/KEY: MOD_RES
<222> LOCATION: (6)..(6)
<223> OTHER INFORMATION: The Xaa is a Cys residue substituted with
      perfluoroquinolin-4-yl.

<400> SEQUENCE: 15

Phe Xaa Gly Gly Gly Xaa Ala Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 16

Phe Xaa Gly Gly Gly Xaa Ala Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      2,3,6-trifluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      2,3,6-trifluoro-pyridin-4-yl.

<400> SEQUENCE: 17

Phe Xaa Gly Gly Gly Xaa Ala Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: MOD_RES
<222> LOCATION: (2)..(2)
<223> OTHER INFORMATION: The Xaa is a Cys residue substituted with
      3,4,6-trichloro-2-fluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      perchloropyridin-2-yl.

<400> SEQUENCE: 18

Phe Xaa Gly Gly Gly Xaa Ala Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      perchloropyridin-2-yl.
<220> FEATURE:
<221> NAME/KEY: MOD_RES
<222> LOCATION: (6)..(6)
<223> OTHER INFORMATION: The Xaa is a Cys residue substituted with
      perchloropyridin-2-yl.

<400> SEQUENCE: 19

Phe Xaa Gly Gly Gly Xaa Ala Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      3,5-dichloro-2,6-difluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      3,5-dichloro-2,6-difluoro-pyridin-4-yl.

<400> SEQUENCE: 20

Phe Xaa Gly Gly Gly Xaa Ala Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.
```

<400> SEQUENCE: 21

Phe Xaa Gly Gly Gly Xaa Ala Leu
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      3-chloro-2,5,6-trifluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      3-chloro-2,5,6-trifluoro-pyridin-4-yl.

<400> SEQUENCE: 22

Phe Xaa Gly Gly Gly Xaa Ala Leu
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      3-chloro-2,5,6-trifluoro-pyridin-4-yl.
<220> FEATURE:
<221> NAME/KEY: MOD_RES
<222> LOCATION: (6)..(6)
<223> OTHER INFORMATION: The Xaa is a Cys residue substituted with
      perfluoropyridin-3-yl.

<400> SEQUENCE: 23

Phe Xaa Gly Gly Gly Xaa Ala Leu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      perfluorophenyl.
<220> FEATURE:
<221> NAME/KEY: MOD_RES
<222> LOCATION: (6)..(6)
<223> OTHER INFORMATION: The Xaa is a Cys residue substituted with
      perfluorophenyl.

<400> SEQUENCE: 24

Phe Xaa Gly Gly Gly Xaa Ala Leu
1               5

<210> SEQ ID NO 25
<211> LENGTH: 8
<212> TYPE: PRT
<213> ORGANISM: Artificial Sequence

```
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 25

Phe Xaa Gly Gly Gly Xaa Ala Leu
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      perfluoropyridin-4-yl.
<220> FEATURE:
<221> NAME/KEY: MOD_RES
<222> LOCATION: (6)..(6)
<223> OTHER INFORMATION: The Xaa is a Cys residue substituted with
      perfluoropyridin-4-yl.

<400> SEQUENCE: 26

Phe Xaa Gly Gly Gly Xaa Ala Leu
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      5-chloro-4,6-difluoro-pyrimidin-2-yl.
<220> FEATURE:
<221> NAME/KEY: MOD_RES
<222> LOCATION: (6)..(6)
<223> OTHER INFORMATION: The Xaa is a Cys residue substituted with
      5-chloro-4,6-difluoro-pyrimidin-2-yl.

<400> SEQUENCE: 27

Phe Xaa Gly Gly Gly Xaa Ala Leu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
```

```
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 28

Phe Xaa Gly Gly Gly Xaa Ala Leu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 29

Phe Xaa Gly Gly Gly Xaa Ala Leu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      perfluoropyridazin-3-yl.

<400> SEQUENCE: 30

Phe Xaa Gly Gly Gly Ser Ala Leu
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      perfluoropyridazin-3-yl.
<220> FEATURE:
<221> NAME/KEY: MOD_RES
<222> LOCATION: (6)..(6)
<223> OTHER INFORMATION: The Xaa is a Ser residue substituted with
      perfluoropyridazin-3-yl.

<400> SEQUENCE: 31

Phe Xaa Gly Gly Gly Xaa Ala Leu
1               5
```

```
<210> SEQ ID NO 32
<211> LENGTH: 8
<212> TYPE: PRT
<213> ORGANISM: Artificial Sequence
<220> FEATURE:
<223

```
<220> FEATURE:
<221> NAME/KEY: MOD_RES
<222> LOCATION: (2)..(2)
<223> OTHER INFORMATION: The Xaa is a Ser residue substituted with
      3,5-dichloro-2,6-difluoro-pyridin-4-yl.
<220> FEATURE:
<221> NAME/KEY: MOD_RES
<222> LOCATION: (6)..(6)
<223> OTHER INFORMATION: The Xaa is a Ser residue substituted with
      3,5-dichloro-2,6-difluoro-pyridin-4-yl.

<400> SEQUENCE: 35

Phe Xaa Gly Gly Gly Xaa Ala Leu
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a  Ser residue substituted with
      2-chloro-3,5,6-trifluoro-pyridin-4-yl.
<220> FEATURE:
<221> NAME/KEY: MOD_RES
<222> LOCATION: (6)..(6)
<223> OTHER INFORMATION: The Xaa is a Ser residue substituted with
      2-chloro-3,5,6-trifluoro-pyridin-4-yl.

<400> SEQUENCE: 36

Phe Xaa Gly Gly Gly Xaa Ala Leu
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      perfluoropyridin-4-yl.
<220> FEATURE:
<221> NAME/KEY: MOD_RES
<222> LOCATION: (6)..(6)
<223> OTHER INFORMATION: The Xaa is a Ser residue substituted with
      perfluoropyridin-4-yl.

<400> SEQUENCE: 37

Phe Xaa Gly Gly Gly Xaa Ala Leu
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      5-chloro-4,6-difluoro-pyrimidin-2-yl.

<400> SEQUENCE: 38

Phe Xaa Gly Gly Gly Ser Ala Leu
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue is substituted with
      5-chloro-4,6-difluoro-pyrimidin-2-yl.
<220> FEATURE:
<221> NAME/KEY: MOD_RES
<222> LOCATION: (6)..(6)
<223> OTHER INFORMATION: The Xaa is a Ser residue is substituted with
      5-chloro-4,6-difluoro-pyrimidin-2-yl.

<400> SEQUENCE: 39

Phe Xaa Gly Gly Gly Xaa Ala Leu
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with a
      phenyl.
<220> FEATURE:
<221> NAME/KEY: MOD_RES
<222> LOCATION: (3)..(3)
<223> OTHER INFORMATION: The Xaa is a Tyr residue substituted with
      4,5,6-trifluoro-pyridazin-3-yl.
<220> FEATURE:
<221> NAME/KEY: MOD_RES
<222> LOCATION: (5)..(5)
<223> OTHER INFORMATION: The Xaa is a Cys residue substituted with a
      phenyl.
<220> FEATURE:
<221> NAME/KEY: MOD_RES
<222> LOCATION: (10)..(10)
<223> OTHER INFORMATION: The Xaa is a Thr residue substituted with
      4,5,6-trifluoro-pyridazin-3-yl.

<400> SEQUENCE: 40

Ala Xaa Xaa Gly Xaa Ile Leu Ala Arg Xaa
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with a
      phenyl.
<220> FEATURE:
<221> NAME/KEY: MOD_RES
<222> LOCATION: (3)..(3)
<223> OTHER INFORMATION: The Xaa is a Tyr residue substituted with
      2,3-difluoro-6-phenylsulfenyl-pyridin-4-yl.

<400> SEQUENCE: 41

Ala Xaa Xaa Gly Ser Ile Leu Ala Arg Thr
1               5                   10
```

```
<210> SEQ ID NO 42
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      2,3,6-trifluoro-pyridin-4-yl.
<220> FEATURE:
<221> NAME/KEY: MOD_RES
<222> LOCATION: (3)..(3)
<223> OTHER INFORMATION: The Xaa is a Tyr residue substituted with
      2,3-difluoro-6-phenylsulfenyl-pyridin-4-yl.

<400> SEQUENCE: 42

Ala Xaa Xaa Gly Ser Ile Leu Ala Arg Thr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      3,4,6-trichloro-5-phenylsulfenyl-pyridin-2-yl.
<220> FEATURE:
<221> NAME/KEY: MOD_RES
<222> LOCATION: (3)..(3)
<223> OTHER INFORMATION: The Xaa is a Tyr residue substituted with
      perchloropyridin-2-yl.
<220> FEATURE:
<221> NAME/KEY: MOD_RES
<222> LOCATION: (5)..(5)
<223> OTHER INFORMATION: The Xaa is a Ser residue substituted with
      perchloropyridin-2-yl.

<400> SEQUENCE: 43

Ala Xaa Xaa Gly Xaa Ile Leu Ala Arg Thr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with a
      substitued heteroaromatic group.
<220> FEATURE:
<221> NAME/KEY: MOD_RES
<222> LOCATION: (3)..(3)
<223> OTHER INFORMATION: The Xaa is a Tyr residue substituted with a
      substitued heteroaromatic group.
<220> FEATURE:
<221> NAME/KEY: MOD_RES
<222> LOCATION: (5)..(5)
<223> OTHER INFORMATION: The Xaa is a Ser residue substituted with a
      substitued heteroaromatic group.

<400> SEQUENCE: 44

Ala Xaa Xaa Gly Xaa Ile Leu Ala Arg Thr
1               5                   10
```

```
<210> SEQ ID NO 45
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with a
      phenyl.
<220> FEATURE:
<221> NAME/KEY: MOD_RES
<222> LOCATION: (3)..(3)
<223> OTHER INFORMATION: The Xaa is a Tyr residue substituted with
      perfluoropyrid-4-yl.

<400> SEQUENCE: 45

Ala Xaa Xaa Gly Ser Ile Leu Ala Arg Thr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with a
      phenyl.
<220> FEATURE:
<221> NAME/KEY: MOD_RES
<222> LOCATION: (3)..(3)
<223> OTHER INFORMATION: The Xaa is a Tyr residue substituted with
      4-fluoro-5,6-di[phenylsulfenyl]-pyrimidin-2-yl.
<220> FEATURE:
<221> NAME/KEY: MOD_RES
<222> LOCATION: (5)..(5)
<223> OTHER INFORMATION: The Xaa is a Ser residue substituted with
      4-fluoro-5,6-di[phenylsulfenyl]-pyrimidin-2-yl.
<220> FEATURE:
<221> NAME/KEY: MOD_RES
<222> LOCATION: (10)..(10)
<223> OTHER INFORMATION: The Xaa is a Thr residue substituted with
      4,6-difluoro-5-chloro-pyrimidin-2-yl.

<400> SEQUENCE: 46

Ala Xaa Xaa Gly Xaa Ile Leu Ala Arg Xaa
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue substituted with
      substituted six-membered ring.
<220> FEATURE:
<221> NAME/KEY: MOD_RES
<222> LOCATION: (3)..(3)
<223> OTHER INFORMATION: The Xaa is a Tyr residue substituted with
      substituted heteroaromatic group.
<220> FEATURE:
<221> NAME/KEY: MOD_RES
<222> LOCATION: (5)..(5)
<223> OTHER INFORMATION: The Xaa is a Ser residue substituted with
      substituted heteroaromatic group.
```

```
<220> FEATURE:
<221> NAME/KEY: MOD_RES
<222> LOCATION: (10)..(10)
<223> OTHER INFORMATION: The Xaa is a Thr residue substituted with
      substituted heteroaromatic group.

<400> SEQUENCE: 47

Ala Xaa Xaa Gly Xaa Ile Leu Ala Arg Xaa
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 48

Phe Xaa Gly Gly Gly Xaa Ala Leu
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Cys residue cyclyated with the
      further Cys residue.
<220> FEATURE:
<221> NAME/KEY: MOD_RES
<222> LOCATION: (6)..(6)
<223> OTHER INFORMATION: The Xaa is a Cys residue cyclyated with the
      further Cys residue.

<400> SEQUENCE: 49

Phe Xaa Gly Gly Gly Xaa Ala Leu
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      substituted heteroaromatic group.

<400> SEQUENCE: 50

Phe Xaa Gly Gly Gly Ser Ala Leu
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      4,5-difluoro-6-hydroxy-pyridazin-3-yl.
<220> FEATURE:
<221> NAME/KEY: MOD_RES
<222> LOCATION: (6)..(6)
<223> OTHER INFORMATION: The Xaa is a Ser residue substituted with
      substituted six-membered ring.

<400> SEQUENCE: 51

Phe Xaa Gly Gly Gly Xaa Ala Leu
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      substituted heteroaromatic group.
<220> FEATURE:
<221> NAME/KEY: MOD_RES
<222> LOCATION: (6)..(6)
<223> OTHER INFORMATION: The Xaa is a Ser residue substituted with
      substituted heteroaromatic group.

<400> SEQUENCE: 52

Phe Xaa Gly Gly Gly Xaa Ala Leu
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      6,7,8-trifluoro-2,3,9-tri[phenylsulfenyl]-quinolin-4-yl.
<220> FEATURE:
<221> NAME/KEY: MOD_RES
<222> LOCATION: (6)..(6)
<223> OTHER INFORMATION: The Xaa is a Ser residue substituted with
      6,7,8-trifluoro-2,3,9-tri[phenylsulfenyl]-quinolin-4-yl.

<400> SEQUENCE: 53

Phe Xaa Gly Gly Gly Xaa Ala Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: MOD_RES
<222> LOCATION: (2)..(2)
<223> OTHER INFORMATION: The Xaa is a Ser residue substituted with
      substituted six-membered ring.
<220> FEATURE:
<221> NAME/KEY: MOD_RES
<222> LOCATION: (6)..(6)
<223> OTHER INFORMATION: The Xaa is a Ser residue substituted with
      substituted heteroaromatic group.

<400> SEQUENCE: 54

Phe Xaa Gly Gly Gly Xaa Ala Leu
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: The Xaa is a Ser residue substituted with
      4,5,6-tri[phenylsulfenyl]-pyrimidin-2-yl.
<220> FEATURE:
<221> NAME/KEY: MOD_RES
<222> LOCATION: (6)..(6)
<223> OTHER INFORMATION: The Xaa is a Ser residue substituted with
      5-chloro-4,6-di[phenylsulfenyl]-pyrimidin-2-yl.

<400> SEQUENCE: 55

Phe Xaa Gly Gly Gly Xaa Ala Leu
1               5
```